(12) United States Patent  
Zilberstein et al.

(10) Patent No.: US 7,970,455 B2  
(45) Date of Patent: Jun. 28, 2011

(54) INGESTIBLE DEVICE PLATFORM FOR THE COLON

(75) Inventors: Yoel Zilberstein, Haifa (IL); Michael Nagler, Tel Aviv (IL); Benny Rousso, Rishon LeZion (IL); Izhar Halahmi, Hod Hasharon (IL)

(73) Assignee: Spectrum Dynamics LLC, Orangeburg, NY (US)

( * ) Notice: Subject to any disclaimer, the term of this patent is extended or adjusted under 35 U.S.C. 154(b) by 1122 days.

(21) Appl. No.: 11/132,320

(22) Filed: May 19, 2005

(65) Prior Publication Data

US 2005/0266074 A1    Dec. 1, 2005

Related U.S. Application Data

(60) Provisional application No. 60/572,466, filed on May 20, 2004.

(51) Int. Cl.
*A61B 6/00* (2006.01)
*A61B 5/05* (2006.01)
*A61B 8/00* (2006.01)

(52) U.S. Cl. ......... 600/436; 600/411; 600/439; 600/476

(58) Field of Classification Search .................. None
See application file for complete search history.

(56) References Cited

U.S. PATENT DOCUMENTS

| | | |
|---|---|---|
| 2,776,377 A | 1/1957 | Anger |
| 3,340,866 A | 9/1967 | Nöller |
| 3,684,887 A | 8/1972 | Hugonin |
| 3,719,183 A | 3/1973 | Schwartz |
| 3,739,279 A | 6/1973 | Hollis |
| 3,971,362 A | 7/1976 | Pope et al. |

(Continued)

FOREIGN PATENT DOCUMENTS

DE 19814199 7/1999

(Continued)

OTHER PUBLICATIONS

Babiar et al. "'Camera Pill' Promising for Diagnosis of Small Bowel Disease", Radiological Society of North America, RSNA, p. 1-3, 2004.

(Continued)

*Primary Examiner* — Long V Le  
*Assistant Examiner* — Angela M Hoffa

(57) ABSTRACT

An ingestible pill platform for colon imaging is provided, designed to recognize its entry to the colon and expand in the colon, for improved imaging of the colon walls. On approaching the external anal sphincter muscle, the ingestible pill may contract or deform, for elimination. Colon recognition may be based on a structural image, based on the differences in diameters between the small intestine and the colon, and particularly, based on the semilunar fold structure, which is unique to the colon. Additionally or alternatively, colon recognition may be based on a functional image, based on the generally inflammatory state of the vermiform appendix. Additionally or alternatively, pH, flora, enzymes and (or) chemical analyses may be used to recognize the colon. The imaging of the colon walls may be functional, by nuclear-radiation imaging of radionuclide-labeled antibodies, or by optical-fluorescence-spectroscopy imaging of fluorescence-labeled antibodies. Additionally or alternatively, it may be structural, for example, by visual, ultrasound or MRI means. Due to the proximity to the colon walls, the imaging in accordance with the present invention is advantageous to colonoscopy or virtual colonoscopy, as it is designed to distinguish malignant from benign tumors and detect tumors even at their incipient stage, and overcome blood-pool background radioactivity.

28 Claims, 20 Drawing Sheets

U.S. PATENT DOCUMENTS

| | | | |
|---|---|---|---|
| 4,278,077 | A | 7/1981 | Mizumoto |
| 4,291,708 | A | 9/1981 | Frei et al. |
| 4,364,377 | A | 12/1982 | Smith |
| 4,458,694 | A | 7/1984 | Sollish et al. |
| 4,674,107 | A | 6/1987 | Urban et al. |
| 4,689,041 | A | 8/1987 | Corday et al. |
| 4,689,621 | A | 8/1987 | Kleinberg |
| 4,773,430 | A | 9/1988 | Porath |
| 4,782,840 | A | 11/1988 | Martin, Jr. et al. |
| 4,801,803 | A | 1/1989 | Denen et al. |
| 4,844,067 | A | 7/1989 | Ikada et al. |
| 4,844,076 | A | 7/1989 | Lesho et al. |
| 4,893,013 | A | 1/1990 | Denen et al. |
| 4,929,832 | A | 5/1990 | Ledley |
| 4,959,547 | A | 9/1990 | Carroll et al. |
| 5,014,708 | A | 5/1991 | Hayashi et al. |
| 5,032,729 | A | 7/1991 | Charpak |
| 5,033,998 | A | 7/1991 | Corday et al. |
| 5,070,878 | A | 12/1991 | Denen |
| 5,115,137 | A | 5/1992 | Andersson-Engels et al. |
| 5,119,818 | A | 6/1992 | Carroll et al. |
| 5,151,598 | A | 9/1992 | Denen |
| 5,170,055 | A | 12/1992 | Carroll et al. |
| 5,170,789 | A | 12/1992 | Narayan et al. |
| 5,246,005 | A | 9/1993 | Carroll et al. |
| 5,279,607 | A | 1/1994 | Schentag et al. |
| 5,284,147 | A | 2/1994 | Hanaoka et al. |
| 5,307,808 | A | 5/1994 | Dumoulin et al. |
| 5,383,456 | A | 1/1995 | Arnold et al. |
| 5,395,366 | A | 3/1995 | D'Andrea et al. |
| 5,399,868 | A | 3/1995 | Jones et al. |
| 5,415,181 | A | 5/1995 | Hogrefe et al. |
| 5,441,050 | A | 8/1995 | Thurston et al. |
| 5,448,073 | A | 9/1995 | Jeanguillaume |
| 5,475,219 | A | 12/1995 | Olson |
| 5,484,384 | A | 1/1996 | Fearnot |
| 5,493,595 | A | 2/1996 | Schoolman |
| 5,572,132 | A | 11/1996 | Pulyer et al. |
| 5,604,531 | A | 2/1997 | Iddan et al. |
| 5,617,858 | A | 4/1997 | Taverna et al. |
| 5,635,717 | A | 6/1997 | Popescu |
| 5,657,759 | A | 8/1997 | Essen-Moller |
| 5,682,888 | A | 11/1997 | Olson et al. |
| 5,690,691 | A | 11/1997 | Chen et al. |
| 5,694,933 | A | 12/1997 | Madden et al. |
| 5,727,554 | A | 3/1998 | Kalend et al. |
| 5,732,704 | A | 3/1998 | Thurston et al. |
| 5,744,805 | A | 4/1998 | Raylman et al. |
| 5,810,742 | A | 9/1998 | Pearlman |
| 5,842,977 | A | 12/1998 | Lesho et al. |
| 5,846,513 | A | 12/1998 | Carroll et al. |
| 5,857,463 | A | 1/1999 | Thurston et al. |
| 5,900,533 | A | 5/1999 | Chou |
| 5,916,167 | A | 6/1999 | Kramer et al. |
| 5,928,150 | A | 7/1999 | Call |
| 5,932,879 | A | 8/1999 | Raylman et al. |
| 5,984,860 | A | 11/1999 | Shan |
| 5,987,350 | A | 11/1999 | Thurston |
| 5,993,378 | A | 11/1999 | Lemelson |
| 6,002,480 | A | 12/1999 | Izatt et al. |
| 6,055,452 | A | 4/2000 | Pearlman |
| 6,082,366 | A | 7/2000 | Andrä et al. |
| 6,107,102 | A | 8/2000 | Ferrari |
| 6,115,635 | A | 9/2000 | Bourgeois |
| 6,132,372 | A | 10/2000 | Essen-Moller |
| 6,135,968 | A | 10/2000 | Brounstein |
| 6,258,576 | B1 | 7/2001 | Richards-Kortum et al. |
| 6,259,095 | B1 | 7/2001 | Bouton et al. |
| 6,280,704 | B1 | 8/2001 | Schutt et al. |
| 6,308,097 | B1 | 10/2001 | Pearlman |
| 6,315,981 | B1 | 11/2001 | Unger |
| 6,324,418 | B1 | 11/2001 | Crowley et al. |
| 6,426,917 | B1 | 7/2002 | Tabanou et al. |
| 6,429,431 | B1 | 8/2002 | Wilk |
| 6,439,444 | B1 | 8/2002 | Shields, II |
| 6,453,199 | B1 | 9/2002 | Kobozev |
| 6,516,213 | B1 | 2/2003 | Nevo |
| 6,607,301 | B1 | 8/2003 | Glukhovsky et al. |
| 6,635,834 | B1 | 10/2003 | Wenner |
| 7,787,926 | B2 * | 8/2010 | Kimchy ........................ 600/407 |
| 2001/0020131 | A1 | 9/2001 | Kawagishi et al. |
| 2001/0035902 | A1 | 11/2001 | Iddan et al. |
| 2002/0072784 | A1 | 6/2002 | Sheppard et al. |
| 2002/0099310 | A1 | 7/2002 | Kimchy et al. |
| 2002/0198470 | A1 | 12/2002 | Imran et al. |
| 2003/0020810 | A1 | 1/2003 | Takizawa et al. |
| 2003/0139661 | A1 | 7/2003 | Kimchy et al. |
| 2003/0191430 | A1 | 10/2003 | D'Andrea et al. |
| 2003/0208107 | A1 * | 11/2003 | Refael ........................ 600/300 |
| 2004/0054278 | A1 * | 3/2004 | Kimchy et al. ............... 600/407 |
| 2004/0162469 | A1 * | 8/2004 | Imran ......................... 600/310 |
| 2005/0075537 | A1 * | 4/2005 | Chen et al. ................... 600/109 |
| 2005/0075555 | A1 * | 4/2005 | Glukhovsky et al. ......... 600/407 |
| 2005/0228293 | A1 * | 10/2005 | Cahill et al. ................. 600/478 |
| 2007/0161885 | A1 * | 7/2007 | Kimchy ........................ 600/407 |

FOREIGN PATENT DOCUMENTS

| | | |
|---|---|---|
| DE | 19815362 | 10/1999 |
| WO | WO 92/00402 | 9/1992 |
| WO | WO 99/03003 | 1/1999 |
| WO | WO 00/31522 | 2/2000 |
| WO | WO 00/18294 | 6/2000 |
| WO | WO 2004/028335 | 4/2004 |
| WO | WO 2005/112895 | 12/2005 |

OTHER PUBLICATIONS

Piperno et al. "Breast Cancer Screening by Impedance Measurements", Frontiers Med. Biol. Engng., 2(2): 11-17, 1990.

Rajshekhar "Continuous Impedence Monitoring During CT-Guided Stereotactic Surgery: Relative Value in Cystic and Solid Lesions", British Journal of Neurosurgery, 6: 439-444, 1992.

Jessup "Tumor Markers—Prognostic and Therapeutic Implications for Colorectal Carcinoma", Surgical Oncology, 7: 139-151, 1998.

Corstens et al. "Nuclear Medicine's Role in Infection and Inflammation", The Lancet, 354: 765-770, 1999.

Mori et al. "Overexpression of Matrix Metalloproteinase-7mRNA in Human Colon Carcinomas", Cancer, 75: 1516-1519, 1995.

Erbil et al. "Use and Limitations of Serum Total and Lipid-Bound Sialic Acid Concentrations as Markers for Colorectal Cancer", Cancer, 55: 404-409, 1985.

Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.

Day et al. "Localization of Radioiodinated Rat Fibrogen in Transplanted Rat Tumors", J. Nat. Cancer Inst., 23: 799-812, 1959.

Jeanguillaume et al. "From the Whole-Body Counting to Imaging: The Computer Aided Collimation Gamma Camera Project (CACAO)", Radiation Projection Dosimetry 89(3-4): 349-352, 2000.

Quartuccia et al. "Computer Assisted Collimation Gama Camera: A New Approach to Imaging Contaminated Tissues", Radiation Projection Dosimetry 89(3-4): 343-348, 2000.

Communication Pursuant to Article 94(3) EPC Dated Mar. 29, 2010 From the European Patent Office Re.: Application No. 05740562.3.

Office Action Dated Dec. 8, 2009 From the US Patent and Trademark Office Re.: U.S. Appl. No. 11/132,320.

Proceedings Further With the European Patent Application Pursuant to Rule 70(2) EPC Dated Jan. 8, 2010 From the European Patent Office Re.: Application No. 05740562.3.

Response Dated Mar. 4, 2010 to Proceedings Further With the European Patent Application Pursuant to Rule 70(2) EPC of Jan. 8, 2010 From the European Patent Office Re.: Application No. 05740562.3.

Supplementary Eurpean Search Report Dated Dec. 22, 2009 From the European Patent Office Re.: Application No. 05740562.

International Search Report and the Written Opinion Dated Apr. 20, 2006 From the International Searching Authority Re.: Application No. PCT/IL05/00517.

Response Dated Dec. 23, 2010 to Communication Pursuant to Article 94(3) EPC of Sep. 3, 2010 From the European Patent Office Re.: Application No. 05740562.3.
Communication Pursuant to Article 94(3) EPC Dated Sep. 3, 2010 From the European Patent Office Re.: Application No. 05740562.3.

Response Dated Jul. 15, 2010 to Communication Pursuant to Article 94(3) EPC of Mar. 29, 2010 From the Eurpoean Patent Office Re.: Application No. 05740562.3.

* cited by examiner

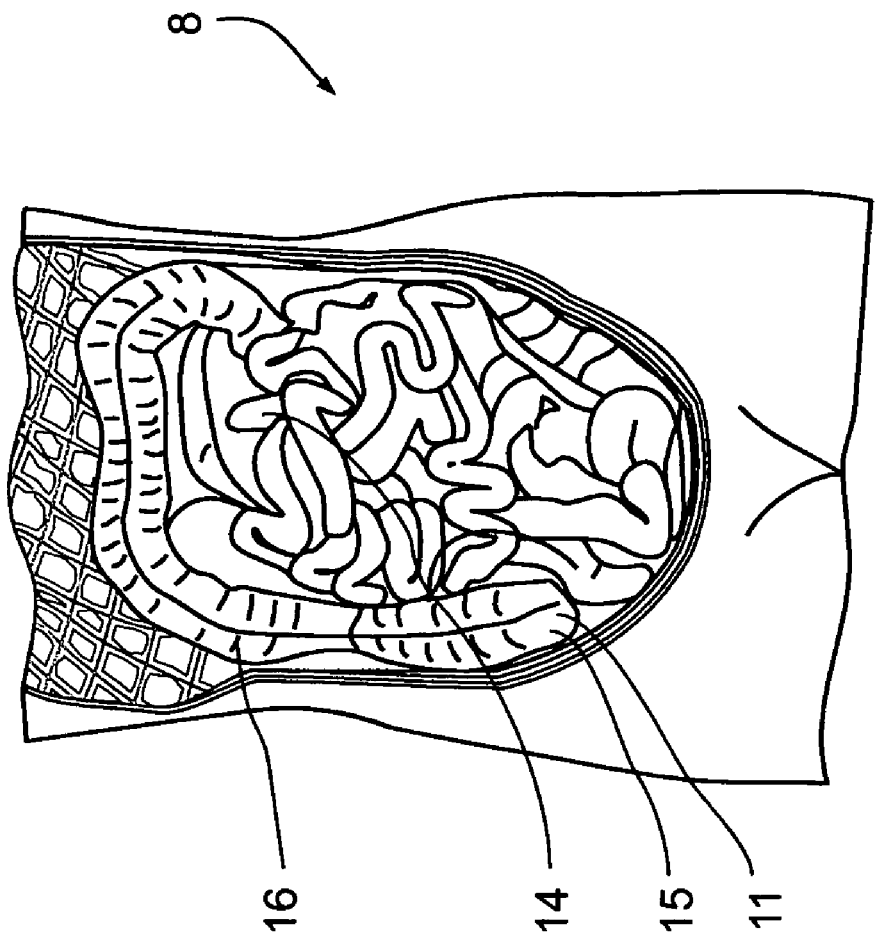

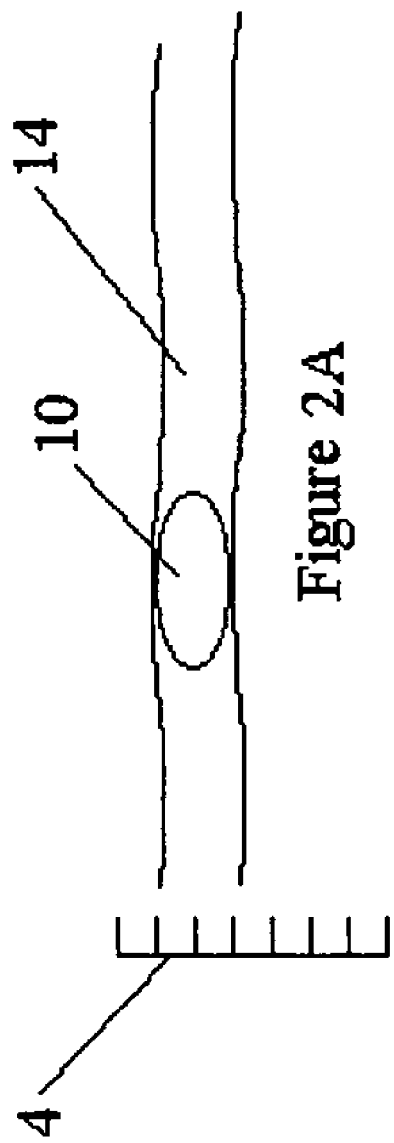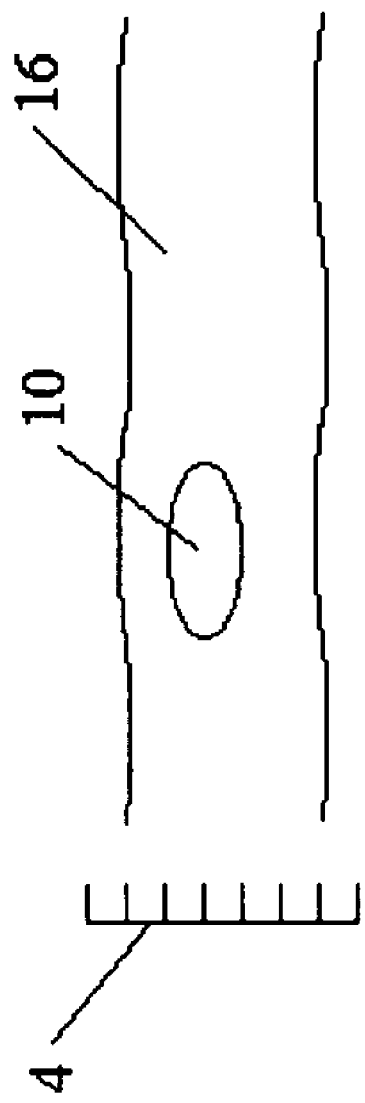

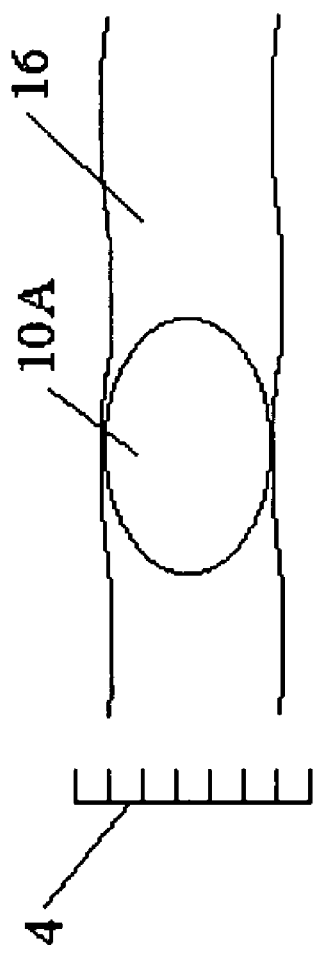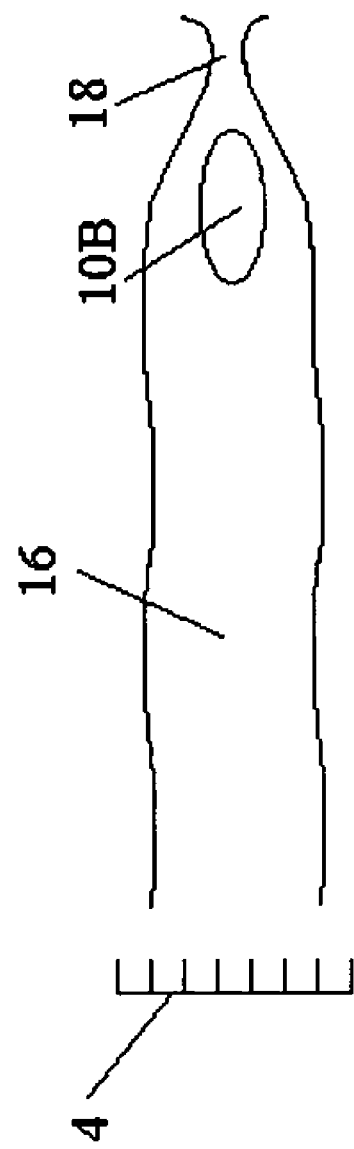

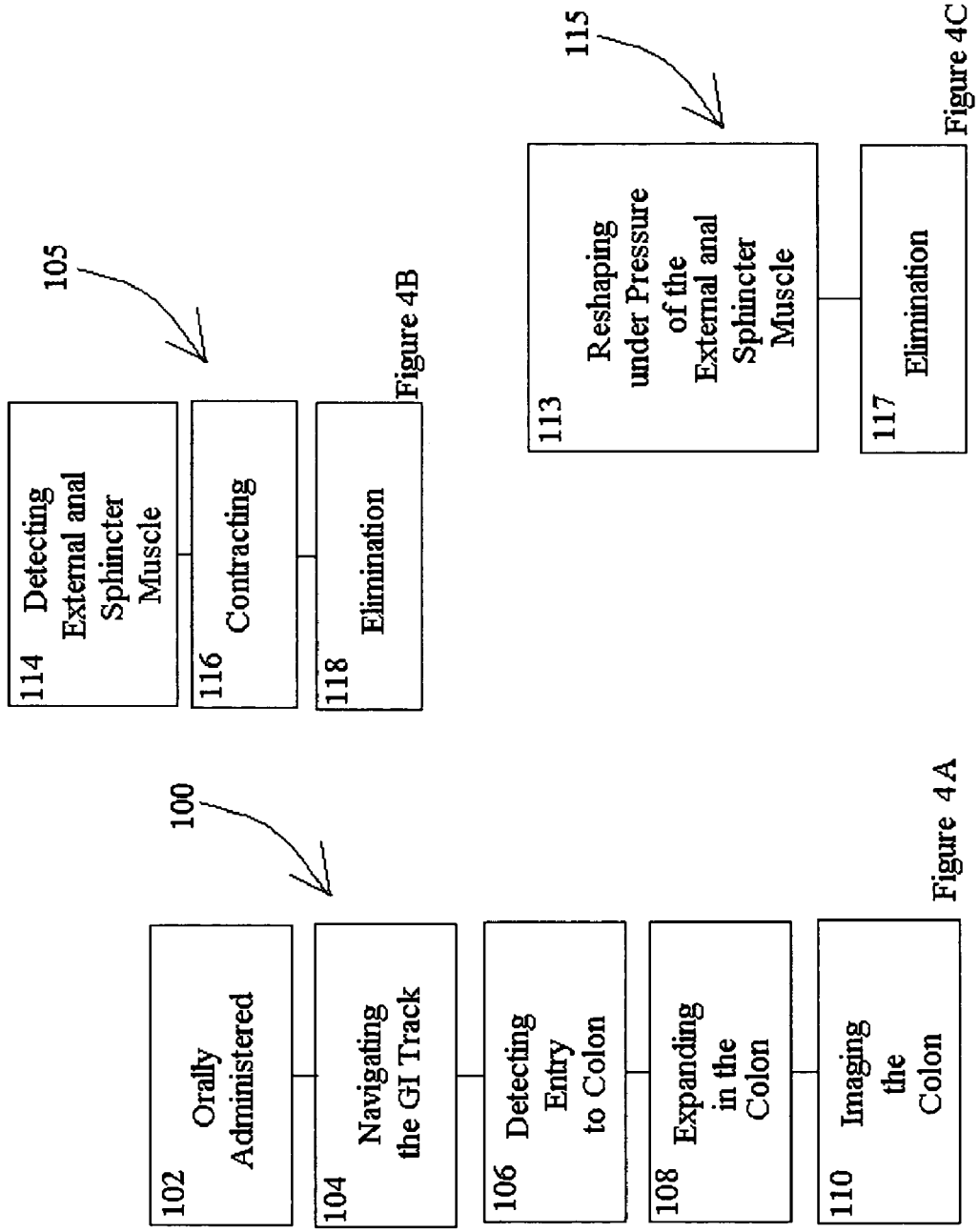

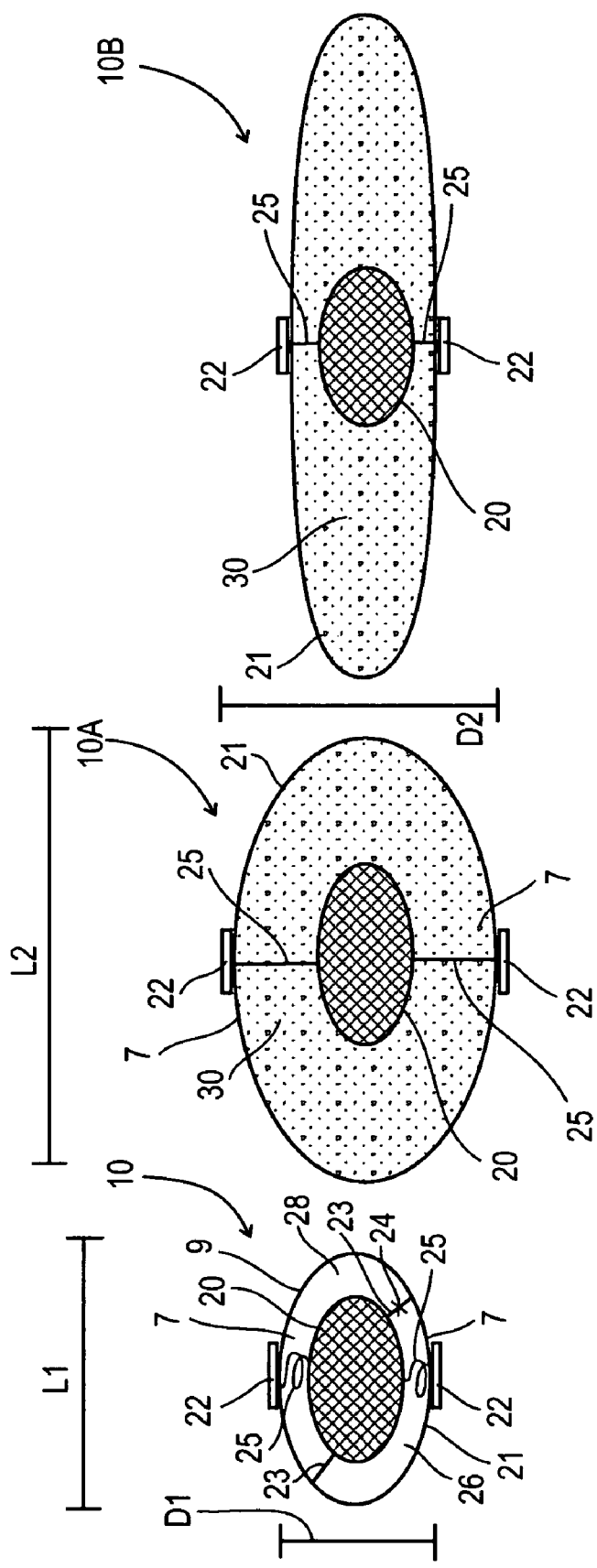

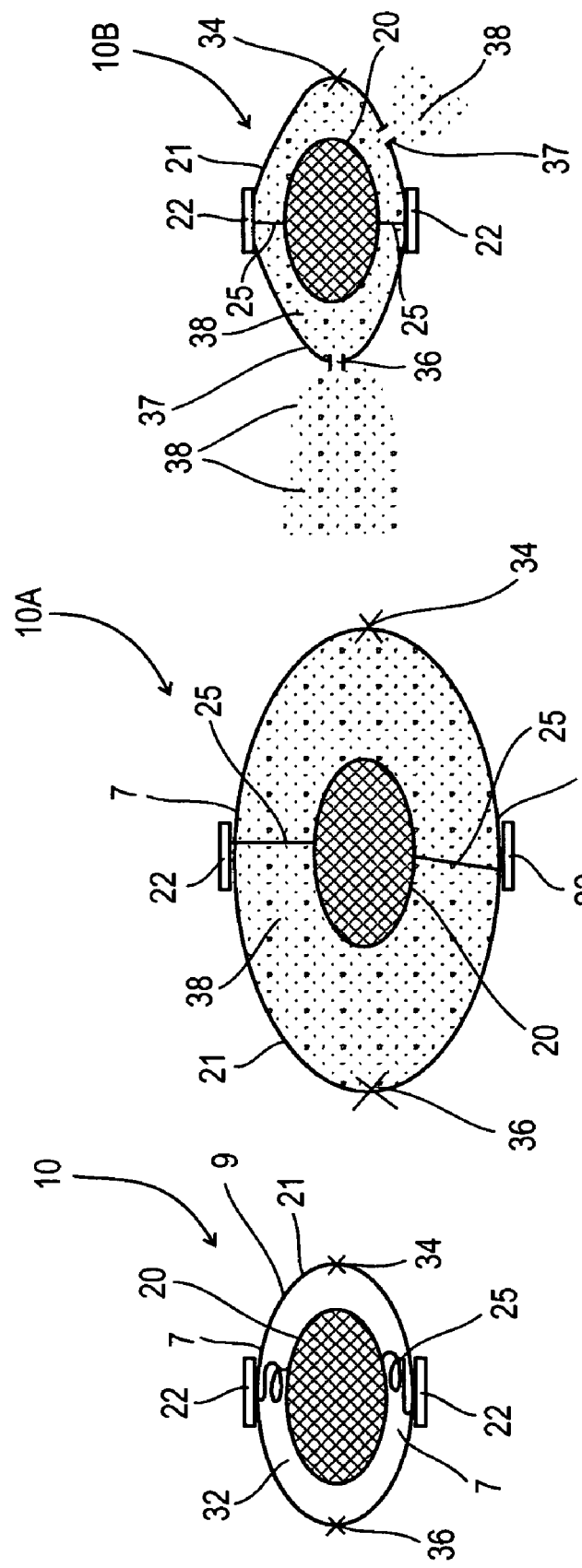

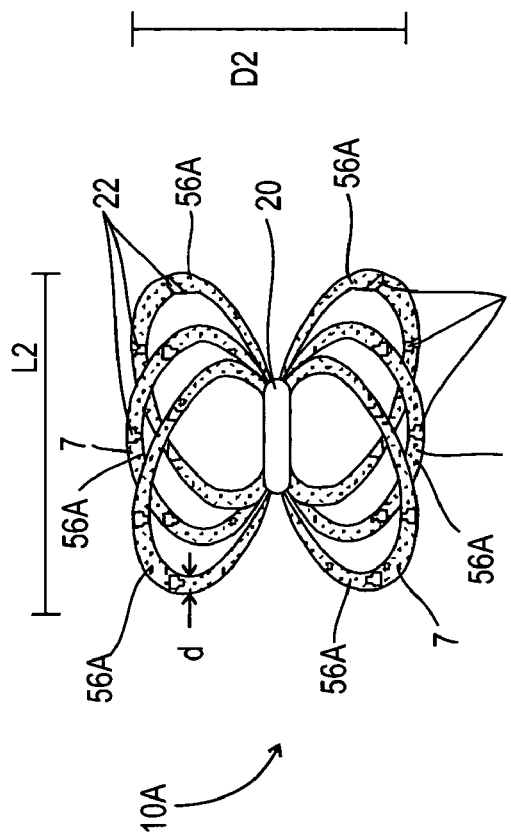
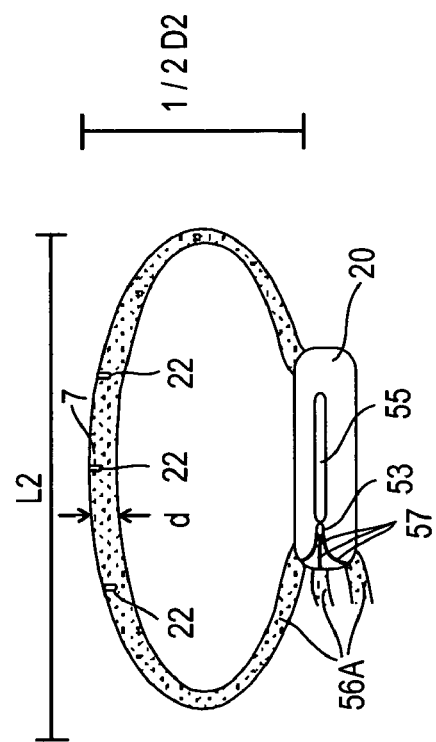
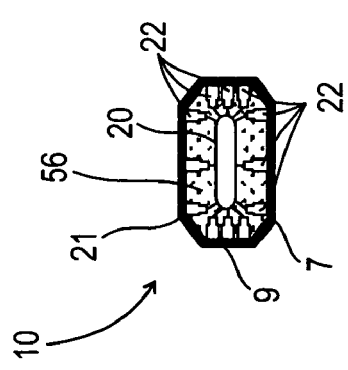
FIG. 5P
FIG. 5Q
FIG. 5O

INGESTIBLE DEVICE PLATFORM FOR THE COLON

CROSS-REFERENCE TO-RELATED APPLICATIONS

The present application derives priority from U.S. Provisional Application 60/572,466, filed on May 20, 2004.

FIELD AND BACKGROUND OF THE INVENTION

The present invention relates to an ingestible pill platform for colon imaging, and more particularly, to an ingestible pill platform, designed to recognize its entry to the colon and designed to expand in the colon, for improved imaging of the colon walls.

The impact of cancer of the gastrointestinal tract is grave. In spite of enormous expenditures of financial and human resources, early detection of malignant tumors remains an unfulfilled medical goal. While it is known that a number of cancers are treatable if detected at an early stage, lack of reliable screening procedures results in their being undetected and untreated.

There are other gastrointestinal-tract disorders, which similarly require reliable screening and diagnostic procedures for early detection and treatment. These include, for example, irritable bowel syndrome, fluxional diarrhea, ulcerative colitis, collagenous colitis, microscopic colitis, lymphocytic colitis, inflammatory bowel disease, Crohn's disease, infectious diarrhea, ulcerative bowel disease, lactase deficiency, infectious diarrhea, amebiasis, and giardiasis.

A large number of techniques are available today for tissue characterization, for example, to determine the presence of abnormal tissue, such as cancerous or pre-cancerous tissue. Many of these may be used with miniature probes that may be inserted into a body lumen.

Tissue Characterization by Nuclear Imaging Nuclear-radiation imaging of radionuclide-labeled antibodies (Gamma Imaging): The use of radiolabeled immunoglobulin for tumor localization, by functional imaging, was shown to be possible in 1959 when Day et al. radiolabeled isolated antifibrin. (Day, E. O.; Planisek, J. A.; Pressman D: "Localization of Radioiodinated Rat Fibrinogen in Transplanted Rat Tumors", J. Natl. Cancer. Inst. 0.23: 799-812, 1959). Since the work of Day et al, in 1959, an expanding number of monoclonal, antibodies have received FDA approval. Examples, applicable to gastrointestinal tract tumors, include the following:
1. CEA-Scan is a $Tc^{99m}$-labeled monoclonal antibody fragment, which targets CEA—produced and shed by colorectal carcinoma cells. The use of anti-CEA, monoclonal antibody has been recommended as the only marker to estimate prognosis and response to therapy. Anti-CEA monoclonal antibody may also be labeled by other radioisotopes, for example, iodine isotopes. (Jessup J M. 1998, Tumor markers—prognostic and therapeutic implications for colorectal carcinoma, Surgical Oncology, 7: 139-151.)
2. $In^{111}$-Satumomab Pendetide (ONCOSCINT®) is designed to target TAG-72. TAG-72 is a mucin-like glycoprotein expressed in human colorectal, gastric, ovarian, breast and lung cancers. It is rarely expressed in normal human adult tissues. (Molinolo A; Simpson JF; et al. 1990, Enhanced tumor binding using immunohistochemical analyses by second generation anti-tumor-associated glycoprotein 72 monoclonal antibodies versus monoclonal antibody B72.3 in human tissue, Cancer Res. 50(4): 1291-8.)
3. Lipid-Associated Sialic Acid (LASA) is a tumor antigen, which for colorectal-carcinoma LASA, has a similar sensitivity as CEA but a greater specificity for differentiating between benign and malignant lesions. (Ebril K M, Jones J D, Klee G G. 1985, Use and limitations of serum total and lipid-bound sialic acid concentrations as markers for colorectal cancer, Cancer; 0.55:404-409.)
4. Matrix Metaloproteinase-7(MMP-7) is a proteins enzyme, believed to be involved in tumor invasion and metastasis. Its expression is elevated in tumor tissue compared to normal tissue and may be a potential marker for tumor aggressiveness and traditional staging. (Mori M, Barnard G F et al. 1995, Overexpression of matrix metalloproteinase-7 mRNA in human colon carcinoma. Cancer; 75: 1516-1519.)

Additionally, pharmaceuticals may be used as markers for nonmalignant pathologies, such as gastrointestinal inflammations and infections. Examples include the following:
1. $Ga^{67}$ citrate binds to transferrin and is used for detection of chronic inflammation. (Mettler F A, and Guiberteau M J, Eds. 1998, Inflammation and infection imaging. Essentials of nuclear medicine. Fourth edition. Pgs: 387-403.)
2. Nonspecific-polyclonal immunoglobulin G (IgG) may be labeled with both $In^{111}$ or $Tc^{99m}$, and has a potential to localize nonbacterial infections. (Mettler F A, and Guiberteau M J, ibid.)
3. Radio-labeled leukocytes, such as such as $In^{111}$ oxine leukocytes and $Tc^{99m}$ HMPAO leukocytes are attracted to sites of inflammation, where they are activated by local chemotactic factors and pass through the endothelium into the soft tissue. Labeled leukocytes in the gastrointestinal tract are nonspecific and may indicate a number of pathologies, including Crohn's disease, ulcerative colitis; psudomembranous colitis, diverticulosis, various gastrointestinal infections, fistulas, ischemic or infracted bowel. (Mettler F A, and Guiberteau M J, ibid; Corstens F H; van der Meer J W. 1999. Nuclear medicine's role in infection and inflammation. Lancet; 354 (9180): 765-70.)

The particular choice of a radionuclide for labeling antibodies is dependent upon its nuclear properties, the physical half-life, the detection instruments' capabilities, the pharmacokinetics of the radiolabeled antibody, and the degree of difficulty of the labeling procedure. Examples of radionuclides used for labeling antibodies include Technetium $Tc^{99m}$, Iodine $I^{125}$, $I^{123}$, $I^{131}$, and $I^{133}$, Indium $In^{111}$, Gallium $Ga^{67}$, thallium $Tl^{201}$, fluorine $F^{18}$ and $P^{32}$.

Nuclear-radiation imaging of radionuclide-labeled antibodies is a subject of continued development and study. Its advantage is that pathologies, which are embedded within a tissue or hidden by residue, may still be visible to the gamma camera, since the gamma rays penetrate the tissue or residue. In fact various means may be employed to calculate the depth of the pathology within the tissue, for example, based on the attenuation of photons of different energies, which are emitted from a same source, as taught by commonly owned U.S. patent application Ser. Nos. 10/616,307 and 10/616,301, both filed on Jul. 10, 2003, and both of whose disclosures are incorporated herein by reference, or by constructing an attenuation correction map for the functional image, based on a structural image, for example, of ultrasound, as taught by commonly owned PCT Patent application PCT/IL03/00917, filed on Nov. 4, 2003, whose disclosure is incorporated herein by reference.

A particular difficulty in using radionuclides is that blood-pool background radioactivity has caused ordinary scintigrams to prove difficult to interpret. Computer subtraction of radioactive blood-pool background radioactivity has been attempted to enhance imaging. Yet the ability to detect occult tumors has remained low.

Attempts to overcome the blood-pool background radioactivity are described, for example, in U.S. Pat. No. 4,782,840 to Martin, Jr., et al., entitled, "Method for locating, differentiating, and removing neoplasms," U.S. Pat. No. 4,801,803 to Denen, et al., entitled, "Detector and localizer for low energy radiation emissions," U.S. Pat. No. 5,151,598 to Denen, entitled, "Detector and localizer for low-energy radiation emissions," U.S. Pat. No. 4,893,013 to Denen et al., entitled, "Detector and Localizer for Low Energy Radiation Emissions," and U.S. Pat. No. 5,070,878 to Denen, entitled, "Detector and localizer for low energy radiation emissions," and U.S. Pat. No. 6,259,095, to Boutun, et al., entitled, "System and apparatus for detecting and locating sources of radiation," all of whose disclosures are incorporated herein by reference, which relate to the RIGS™. (RIGS is a registered trademark of Neoprobe Corporation of Dublin, Ohio), and to "NEOPROBE" instrument.

In spite of these advances, background radiation remains an obstacle that limits the probe sensitivity to occult tumors, and there are continued endeavors to minimize its effect.

Tissue Characterization by Ultrasonography: Ultrasonography is a medical imaging technique, using high frequency sound waves in the range of about 1 to 20 MHz and their echoes. The sound waves travel in the body and are reflected by interfaces between different types of tissues, such as between a healthy tissue and a denser cancerous tissue, or between a portion of a soft tissue and a bone. The ultrasound probe receives the reflected sound waves and the associated instrumentation calculates the distances from the probe to the reflecting boundaries.

The ultrasound probe includes a piezoelectric crystal, which produces an electric signal in response to a pressure pulse. The shape of the probe determines its field of view, and the frequency of the emitted sound determines the minimal detectable object size. Generally, the probes are designed to move across the surface of the body. However, some probes are designed to be inserted through body lumens, such as the vagina or the rectum, so as to get closer to the organ being examined.

Before the early 1970's ultrasound imaging systems were able to record only the strong echoes arising from the outlines of an organ, but not the low-level echoes of the internal structure. In 1972 a refined imaging mode was introduced called gray-scale display, in which the internal texture of many organs became visible. In consequence, ultrasound imaging became a useful tool for imaging tumors, for example, in the liver.

Contrast agents may be used in conjunction with ultrasound imaging, for example as taught by U.S. Pat. No. 6,280,704, to Schutt, et al., entitled, "Ultrasonic imaging system utilizing a long-persistence contrast agent,"whose disclosure is incorporated herein by reference.

Tissue Characterization by Electrical Impedance Imaging: Electrical impedance imaging relates to measuring the impedance between a point on the surface of the skin and some reference point on the body of a patient. Sometimes, a multi-element probe, formed as a sheet having an array of electrical contacts, is used for obtaining a two-dimensional impedance map of the tissue, for example, the breast. The two-dimensional impedance map may be used, possibly in conjunction with other data, such as mammography, for the detection of cancer.

Rajshekhar, V. ("Continuous impedance monitoring during CT-guided stereotactic surgery: relative value in cystic and solid-lesions," Rajshekhar, V., British Journal of Neurosurgery, 1992, 6, 439-444) describes using an impedance probe with a single electrode to measure the impedance characteristics of lesions. The objective of the study was to use the measurements made in the lesions to determine the extent of the lesions and to localize the lesions more accurately. The probe was guided to the tumor by CT and four measurements were made within the lesion as the probe passed through the lesion. A biopsy of the lesion was performed using the outer sheath of the probe as a guide to position, after the probe itself was withdrawn.

Other work in impedance probes includes U.S. Pat. No. 4,458,694, to Sollish, et al., entitled, "Apparatus and method for detection of tumors in tissue," U.S. Pat. No. 4,291,708 to Frei, et al., entitled, "Apparatus and method for detection of tumors in tissue," and U.S. Pat. Nos. 6,308,097, 6,055,452 and 5,810,742, to Pearlman, A. L., entitled, "Tissue characterization based on impedance images and on impedance measurements," all of whose disclosures are incorporated herein by reference.

Tissue Characterization by Optical Fluorescence Spectroscopy: When a sample of large molecules is irradiated, for example, by laser light, it will absorb radiation, and various levels will be excited. Some of the excited states will return back substantially to the previous state, by elastic scattering, and some energy will be lost in internal conversion, collisions and other loss mechanisms. However, some excited states will create fluorescent radiation, which, due to the distribution of states, will give a characteristic wavelength distribution.

Some tumor-marking agents give well-structured fluorescence spectra, when irradiated by laser light. In particular, hematoporphyrin; derivatives. (HPD), give a well-structured fluorescence spectrum, when excited in the Soret band around 405 rim. The fluorescence spectrum-shows typical peaks at about 630 and 690 nm, superimposed in practice on more unstructured tissue autofluorescence. Other useful tumor-marking agents are dihematoporphyrin ether/ester (DHE), hematoporphyrin (HP), polyhematoporphyrin ester (PHE), and tetrasulfonated phthalocyanine (TSPC), when irradiated at 337 nm ($N_2$ laser).

U.S. Pat. No. 5,115,137, to Andersson-Engels, et al, entitled, "Diagnosis by means of fluorescent light emission from tissue," whose disclosure is incorporated herein by reference, relates to improved detection of properties of tissue by means of induced fluorescence of large molecules. The tissue character may then be evaluated from the observed large-molecule spectra. According to U.S. Pat. No. 5,115,137, the spectrum for tonsil cancer is clearly different from normal mucosa, due to endogenous porphyrins.

U.S. Pat. No. 6,258,576, to Richards-Kortum, et al., entitled, "Diagnostic method and apparatus for cervical squamous intraepithelial lesions in vitro and in vivo using fluorescence spectroscopy," whose disclosure is incorporated herein by reference, relates to the use of multiple illumination wavelengths in fluorescence spectroscopy for the diagnosis of cancer and precancer, for example, in the cervix. In this manner, it has been possible to (i) differentiate normal or inflamed tissue from squamous intraepithelial lesions (SILs) and (ii) differentiate high grade SILs from, non-high grade SILs. The detection may be performed in vitro or in vivo. Multivariate statistical analysis has been employed to reduce the number of fluorescence excitation-emission wavelength pairs needed to redevelop algorithms that demonstrate a minimum decrease in classification accuracy. For example, the method of the aforementioned patent may comprise illuminating a tissue sample, with electromagnetic radiation wavelengths of about 337 nm, 380 nm and 460 nm, to produce fluorescence; detecting a plurality of discrete emission wavelengths from the fluorescence; and calculating from the emission wavelengths a probability that the tissue sample belongs in particular tissue classification.

U.S. Patent Application 2003/01383786, to Hashimshony, entitled, "Method and apparatus for examining tissue for predefined target cells, particularly cancerous cells, and a probe useful for such method and apparatus,"whose disclosure is incorporated herein by reference, teaches a method apparatus and probe for examining tissue and characterizing its type according to measured changes in optical characteristics of the examined tissue. In a preferred embodiment of this method the tissue to be examined is subject to a contrast agent containing small particles of a physical element conjugated with a biological carrier selectively bindable to the target cells. Additionally, energy pulses are applied to the examined tissue, and the changes in impedance and/or the optical characteristics produced by the applied energy pulses are detected and utilized for determining the presence of the target cells in the examined tissue. Furthermore, in a preferred embodiment, the applied energy pulses include laser pulses, and the physical element conjugated with a biological carrier is a light-sensitive semiconductor having an impedance which substantially decrease in the presence of light. Moreover, the same probe used for detecting the targeted cells, may also be used for destroying the 'cells' so targeted.

Tissue Characterization by Optical Reflective Spectroscopy: The application optical reflectance spectroscopy for tissue characterization is described, for example, in http://www.sbsp-limb.nichd.nih.gov/html/spectroscopy.html, downloaded on Mar. 15, 2005, disclosing an optical reflectance spectroscopy (ORS) device for measuring the thickness of the epithelial layer, and an evaluation technique based on oblique angle reflectance spectroscopy, that allows assessment of the scattering and absorption properties of the epithelium and stroma, thus providing information on chronic oral epithelial tissue inflammation, which is considered a potential diagnostic precursor to oral cancer.

Additionally, Tomatis, A., et al, studied reflectance images of 43 pigmented lesions of the skin (18 melanomas, 17 common melanocytic naevi and eight dysplastic naevi). Reflectance images were acquired by a telespectrophotometric system and were analyzed in the spectral range from 420 to 1040 nm, to discriminate melanoma from benign melanocytic entities. Different evaluations were carried, out considering the whole spectrum, the visible and the near infrared. A total of 33 (76.7%) lesions were correctly diagnosed by the telespectrophotometric system, compared with 35 (81.4%) correct clinical diagnoses. Reflectance in the infrared band appears diagnostically relevant.

Tissue Characterization by Magnetic Resonance Imaging (MRI): Magnetic resonance imaging is based on the absorption and emission of energy in the radio frequency range of the electromagnetic spectrum, by nuclei having unpaired spins.

Conventional MRI is a large-apparatus, for whole body imaging, having:
i. a primary magnet, which produces the $B_o$ field for the imaging procedure;
ii. gradient coils for producing a gradient in $B_o$;
iii. an RF coil, for producing the $B_1$ magnetic field, necessary to rotate the spins by 90° or 180° and, for detecting the MRI signal; and
iv. a computer, for controlling the components of the MRI imager Generally, the magnet is a large horizontal bore superconducting magnet, which provides a homogeneous magnetic field in an internal region within the magnet, A patient or object to be imaged is usually positioned in the homogeneous field region located in the central air gap for imaging. A typical gradient coil system comprises an anti-Helmholtz type of coil. These are two Parallel ring shaped coils, around the z axis. Current in each of the two coils flows in opposite directions creating a magnetic field gradient between the two coils.

The RF coil creates a $B1$ field, which rotates the net magnetization in a pulse sequence. The RF coils may be: 1) transmit and receive coils, 2) receive only coils, and 3) transmit only coils.

As described hereinabove, the MRI relies on a magnetic field in an internal region within the magnet. As such, it is unsuitable as a handheld probe or an endoscopic probe, because the tissue to be imaged has to be in the internal region of the imager, However, U.S. Pat. No. 5,572,132, to Pulyer, et al., entitled, "MRI probe for external imaging," whose disclosure is incorporated herein by reference, describes an MRI spectroscopic probe having an external background magnetic field $B0$ (as opposed to the internal background magnetic filed of the large horizontal bore superconducting magnet.). Thus, an MRI catheter for endoscopical imaging of tissue of the artery wall, rectum, urinal tract, intestine, esophagus, nasal passages, vagina and other biomedical applications may be constructed. The probe comprises (i) a miniature primary magnet having a longitudinal axis and an external surface extending in the axial direction, and (ii) a RF coil surrounding and proximal to said surface. The primary magnet is structured and configured to provide a symmetrical, preferably cylindrically shaped, homogeneous field region external to the surface of the magnet. The RF coil receives NMR signals from excited nuclei. For imaging, one or more gradient coils are provided to spatially encode the nuclear spins of nuclei excited by an RF coil, which may be the same coil used for receiving NMR signals or another RF coil.

Contrast agents may be used in conjunction with MRI For example, U.S. Pat. No. 6,315,981 to Unger, entitled, "Gas filled microspheres as magnetic-resonance imaging contrast agents," whose disclosure is incorporated herein by reference; describes the use of gas filled microspheres as contrast agents for MRI; Unger further describes how gas can be used in combination with polymer compositions and possibly also with paramagnetic, superparamagnetic, and liquid fluorocarbon compounds as MRI contrast agents. It is further shown how: the gas stabilized by polymers would function as an effective susceptibility contrast agent to decrease signal intensity on T2 weighted images; and that such systems are particularly effective for use as gastrointestinal MRI contrast media Additionally, when MRI contrast agents are tied up to antibodies, the MRI may be used as a functional imaging technique. The MRI contrast agent may be a solution of Gd-dtpa, prepared for injection.

Tissue Characterization by Temperature Imaging: Temperature Imaging for locating and detecting neoplastic tissue has been known, since the 1950's, when it was discovered that the surface temperature of skin in the area of a malignant tumor exhibited a higher temperature than that expected of healthy tissue. Thus, by measuring body skin temperatures, it became possible to screen for the existence of abnormal body activity such as cancerous tumor growth. With the development of liquid crystals and methods of forming temperature responsive chemical substrates, contact thermometry became a reality along with its use in medical applications. Devices employing contact thermometry could sense and display temperature changes through indicators, which changed colors, either permanently or temporarily, when placed in direct physical contact with a surface such as skin, reflecting a temperature at or near the point of contact. An abnormal reading would alert a user to the need for closer, more detailed examination of the region in question. However, the art in this area has been directed primarily at sensing and displaying temperatures on exterior skin surfaces.

U.S. Pat. No. 6,135,968, to Brounstein, entitled, "Differential temperature measuring device and method", whose disclosure is incorporated herein by reference, describes a device and method for sensing temperatures at internal body locations non-surgically accessible only through body orifices. The device is particularly useful in medical applications such as screening for cancer and other abnomial biological activity signaled by an increase in temperature at a selected site.

Ingestible Pills: Ingestible radio pills, which are ingestible capsules containing a transmitter are known. In 1964 research at Heidelberg University developed a pill for monitoring pH of the gastrointestinal tract. (Noller, H. G., "The Heidelberg Capsule Used For the Diagnosis of Pepic Diseases", Aerospace Medicine, February, 1964, pp. 15-117.)

U.S. Pat. No. 5,604,531; to Iddan, et al., entitled, "In vivo video camera system," whose, disclosure is incorporated herein by reference, describes a video camera system, encapsulated within an ingestible pill, arranged to pass through the entire digestive tract, operating as an autonomous video endoscope. The ingestible pill includes a camera system and an optical system for imaging an area of interest onto the camera system, and a transmitter, which relays the video output of the camera system to an extracorporeal reception system. A light source is located within a borehole of the optical system.

Similarly, U.S. Patent Application 20010035902, to Iddan, G. J., et al., entitled, "Device and system for in vivo imaging," whose disclosure is incorporated herein by reference, describes a system and method for obtaining in vivo images. The system contains an imaging system and an ultra low-power radio frequency transmitter for transmitting signals from the CMOS imaging camera to a receiving system located outside a patient. The imaging system includes at least one CMOS imaging camera, at least one illumination source for illuminating an in vivo site and an optical system for imaging the in vivo site onto the CMOS imaging camera.

U.S. Pat. No. 6,324,418, to Crowley, et al., entitled, "Portable tissue spectroscopy apparatus and method,." whose disclosure is incorporated herein by reference, describes a portable tissue spectroscopy apparatus including at least one light source, at least one light detector, a power source and a controller module, all disposed inside a housing that is insertable inside a body. The housing may be in the form of a hand-holdable probe or in the form of a capsule that can be swallowed or implanted in the body. The probe further includes a display mounted at a proximal end of the housing for displaying tissue characteristics. The capsule further includes a transmitter mounted inside the capsule and a receiver placed outside the body for transmitting signals representative of tissue characteristics to a remote receiver.

The capsule includes one or more light emitters and one or more light detectors. The light detectors may be located in various places within the housing for detecting spectroscopic properties from various tissues near the capsule. The capsule may further include other types of emitters and sensors. The additional emitters and sensors, for example, can relate to electromagnetic radiation; pressure, temperature, x-ray radiation and/or heat. In one embodiment, the capsule further comprises an acoustic transmitter and a receiver for measuring flow of fluid or for detecting echo location of the capsule. In another embodiment, the capsule further includes diagnostic sensors such as monitoring electrodes, pressure sensors and temperature sensors.

Methods of tracking ingestible devices, such as radio pills, are known. U.S. Pat. No. 5,279,607, to Schentag, et al., entitled, "Telemetry capsule and process," and U.S. Pat. No. 5,395,366, to D'Andrea et al. entitled, "Sampling capsule and process," described hereinabove, include extracorporeal apparatus having a plurality of antennae, used to determine the geographic position of the capsule within the gastrointestinal tract. For example, at least three antennae, located at different distances from the point source, and dedicated algorithms may be used to determine the precise location of the capsule, at any time.

U.S. Pat. No. 6,082,366 to Andrii et al., entitled, "Method and arrangement for determining the position of a marker in an organic cavity," whose disclosure is incorporated herein by reference, describe a method for pinpointing a marker such as an ingestible capsule. The method requires that the patient be positioned within a magnetic field, for example, as used for MRI imaging.

Commonly owned U.S. Patent Application 20030139661, to Kimchy et al., entitled, "Ingestible pill," whose disclosure is incorporated herein by reference describes an ingestible device, adapted to travel in the gastrointestinal tract and perform a diagnostic image of tissue therein. The diagnostic image may comprise diagnostic information as a function of time, or diagnostic information as a function of distance traveled within the gastrointestinal tract. Specifically, the ingestible device may be arranged to perform a diagnostic image of nuclear radiation of a radiopharmaceutical, scintillation of a scintillation liquid, responsive to nuclear radiation of a radiopharmaceutical, optical fluorescence of a fluorescing-pharmaceutical or of bare gastrointestinal-tract tissue, infrared radiation of the gastrointestinal-tract tissue, temperature-differences along the gastrointestinal-tract, impedance, ultrasound reflection, magnetic resonance, and a combination thereof. The ingestible device may be adapted for general screening of a large population, on the one hand, and for specific diagnoses of suspected pathologies, on the other.

Additionally, commonly owned U.S. Patent Application. 20040054278, to Kimchy, et al., entitled "Ingestible device," describes a device, adapted to travel in the gastrointestinal tract and perform a diagnostic image of tissue therein. The diagnostic image may comprise diagnostic information as a function of time, or diagnostic information as a function of distance traveled within the gastrointestinal tract. An imaging method by depth calculations is provided, based on the attenuation of photons of different energies, which are emitted from the same source, coupled with position monitoring.

Notwithstanding the high level of sophistication of the aforementioned systems, gastrointestinal pathologies, and particularly, occult tumors have remained elusive in medical diagnosis. There is thus a widely recognized need for, and it would be highly advantageous to have, a device and method for detecting pathologies in the gastrointestinal tract devoid of the above limitations.

SUMMARY OF THE INVENTION

According to one aspect of the present invention, there is thus provided an ingestible pill, adapted for detecting pathologies in a colon and comprising:

an initial volume, having initial length and width parameters and a center of volume, said initial volume being sized for swallowing by a body;

an external region, forming an outer perimeter of said initial volume;

at least one detector, located in said external region, for detecting pathologies in said colon;

a trigger mechanism, located in said ingestible pill and designed to trigger upon reaching an environment unique to said colon; and an expansion mechanism, designed to expand said ingestible pill into an expanded structure, having expanded length and width parameters, which are between a factor of two and a factor of five greater than said initial length and width parameters, so as to push said external-region in an outward direction from said center of volume, when said trigger mechanism triggers.

According to another aspect of the present invention, there is thus provided an ingestible pill, adapted to electronically detect entry to a colon, comprising:

an initial volume, having initial length and width parameters, sized for swallowing by a body;

at least one detector, adapted to produce an electronic signal, upon entry of said colon.

According to still another aspect of the present invention, there is thus provided a method of detecting pathologies in a colon, comprising:

ingesting an ingestible pill, adapted for detecting pathologies in a colon, wherein said ingestible pill comprises:

an initial volume, having initial length and width parameters and a center of volume, said initial volume being sized for swallowing by a body;

an external region, forming an outer perimeter of said initial volume;

at least one detector, located in said external region, for detecting pathologies in said colon;

a trigger mechanism, designed to trigger upon reaching an environment unique to said colon; and an expansion mechanism, designed to expand said ingestible pill into an expanded structure, having expanded length and width parameters, which are between a factor of two and a factor of five greater than said initial length and width parameters, so as to push said external region in an outward direction from said center of volume, when said trigger mechanism triggers; and detecting pathologies in a colon, by said at least one detector, located in said external region, after said ingestible pill has expanded to said expanded structure.

According to yet another aspect of the present invention, there is thus provided a method of detecting pathologies in a colon, comprising:

ingesting a ingestible pill, adapted for detecting pathologies in a colon, wherein said ingestible pill comprises:

an initial volume, having initial length and width parameters, sized for swallowing by a body;

at least one detector, located at an outer region of said ingestible pill, adapted to produce an electronic signal, upon entry of said colon;

an electronic trigger, which triggers an expansion mechanism, designed to expand said ingestible pill into an expanded structure, having expanded length and width parameters, which are between a factor of two and a factor of five greater than said initial length and width parameters, responsive to said electronic signal; and detecting pathologies in a colon, by said at least one detector, located in said external region, after said ingestible pill has expanded to said expanded structure.

According to still another aspect of the present invention, there is thus provided a method of detecting pathologies in a colon comprising:

ingesting a ingestible pill, adapted for detecting pathologies in a colon, wherein said ingestible pill comprises:

an initial volume, having initial length and width parameters, sized for swallowing by a body, at least one detector, adapted to produce an electronic signal, upon entry of said colon;

an electronic trigger, which triggers an expansion mechanism, designed to expand said ingestible pill into an expanded structure, having expanded length and width parameters, which are between a factor of two and a factor of five greater than said initial length and width parameters, responsive to said electronic signal; and at least one second detector, located at an outer region of said ingestible pill and adapted to detect pathologies in said colon; and detecting pathologies in a colon, by said, at least one second detector, located in said external region, after said ingestible pill has expanded to said expanded structure.

The present invention successfully addresses the shortcomings of the presently known configurations by providing an ingestible pill platform for colon imaging Specially, the ingestible pill platform is designed to recognize its entry to the colon and expand in the colon, for improved imaging of the colon walls. On approaching the external anal sphincter muscle, the ingestible pill may contract or deform, for elimination. Colon recognition may be based on a structural image, based on the differences in structure between the small intestine and the colon, and particularly, based on the semilunar fold structure, which is unique to the colon. Additionally or alternatively, colon recognition may be based on a functional image, based on the generally inflammatory state of the vermiform appendix. Additionally or alternatively, pH, flora, enzymes and (or) chemical analyses may be used to recognize the colon. The imaging of the colon walls may be functional, by nuclear-radiation imaging of radionuclide-labeled antibodies, or by optical-fluorescence-spectroscopy imaging of fluorescence-labeled antibodies. Additionally or alternatively, it may be structural, for example, by visual, ultrasound or MRI means. Due to the proximity to the colon walls, the imaging in accordance with the present invention is advantageous to colonoscopy or virtual colonoscopy, as it is designed to distinguish malignant from benign tumors and detect tumors even at their incipient stage, and overcome blood-pool background radioactivity.

Implementation of the methods and systems of the present invention involves performing or completing selected tasks or steps manually, automatically, or a combination thereof. Moreover, according to actual instrumentation and equipment of preferred embodiments of the methods and systems of the present invention, several selected steps could be implemented by hardware or by software on any operating system of any firmware or a combination thereof. For example, as hardware, selected steps of the invention could be implemented as a chip a circuit. As software, selected steps of the invention could be implemented as a plurality of software instructions being executed by a computer using any suitable algorithms. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1C schematically illustrate, the gastrointestinal tract of a stomach;

FIGS. 2A-2B schematically illustrate an ingestible pill, navigating its way along a small intestine and along a colon;

FIGS. 3A-3B schematically illustrate an ingestible pill, which expands in the colon, for colon imaging, and which contracts on approaching the external anal sphincter muscle, for elimination, in accordance with the present invention;

FIGS. 4A-4C schematically illustrate, in flowchart forms, operational steps, using ingestible pills, according to the present invention;

DESCRIPTION OF THE PREFERRED EMBODIMENTS

Figure 1B:
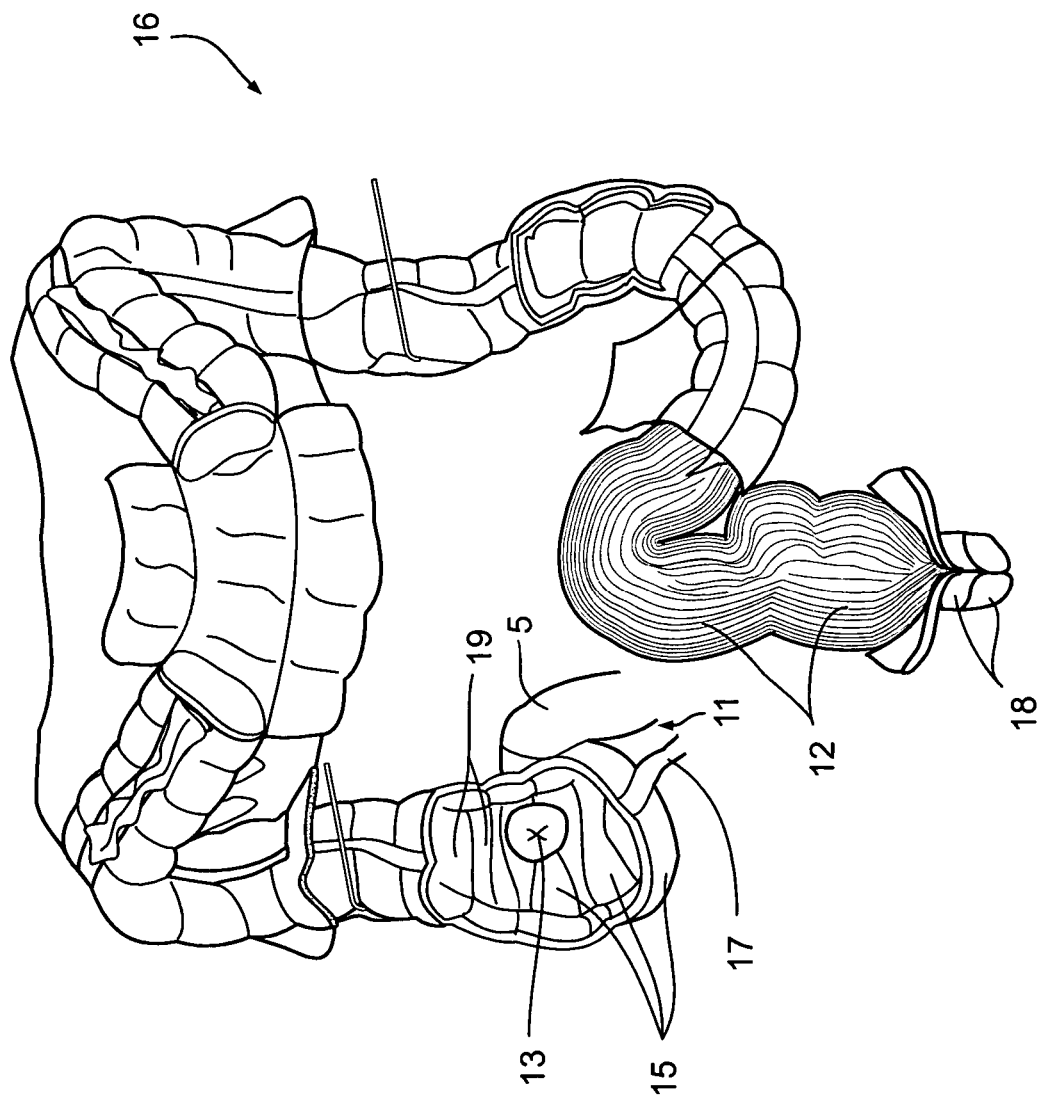

The present invention is of an ingestible pill platform for colon imaging. Specially, the ingestible pill platform is designed to recognize its entry to the colon and expand in the colon, for improved imaging of the colon walls. On approaching the external anal sphincter muscle, the ingestible pill may contract or deform, for elimination. Colon recognition may be based on a structural image, based on the differences in structure between the small intestine and the colon, and particularly, based on the semilunar fold structure, which is unique to the colon. Additionally or alternatively, colon recognition may be based on a functional image, based on the generally inflammatory state of the vermiform appendix. Additionally or alternatively, pH, flora, enzymes and (or) chemical analyses may be used to recognize the colon. The imaging of the colon walls may be functional, by nuclear-radiation imaging of radionuclide-labeled antibodies, or by optical-fluorescence-spectroscopy imaging of fluorescence-labeled antibodies. Additionally or alternatively, it may be structural, for example, by visual, ultrasound or MRI means. Due to the proximity to the colon walls, the imaging in accordance with the present invention is advantageous to colonoscopy or virtual colonoscopy, as it is designed to distinguish malignant from benign tumors and detect tumors even at their incipient stage, and overcome blood-pool background radio-activity.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1C:
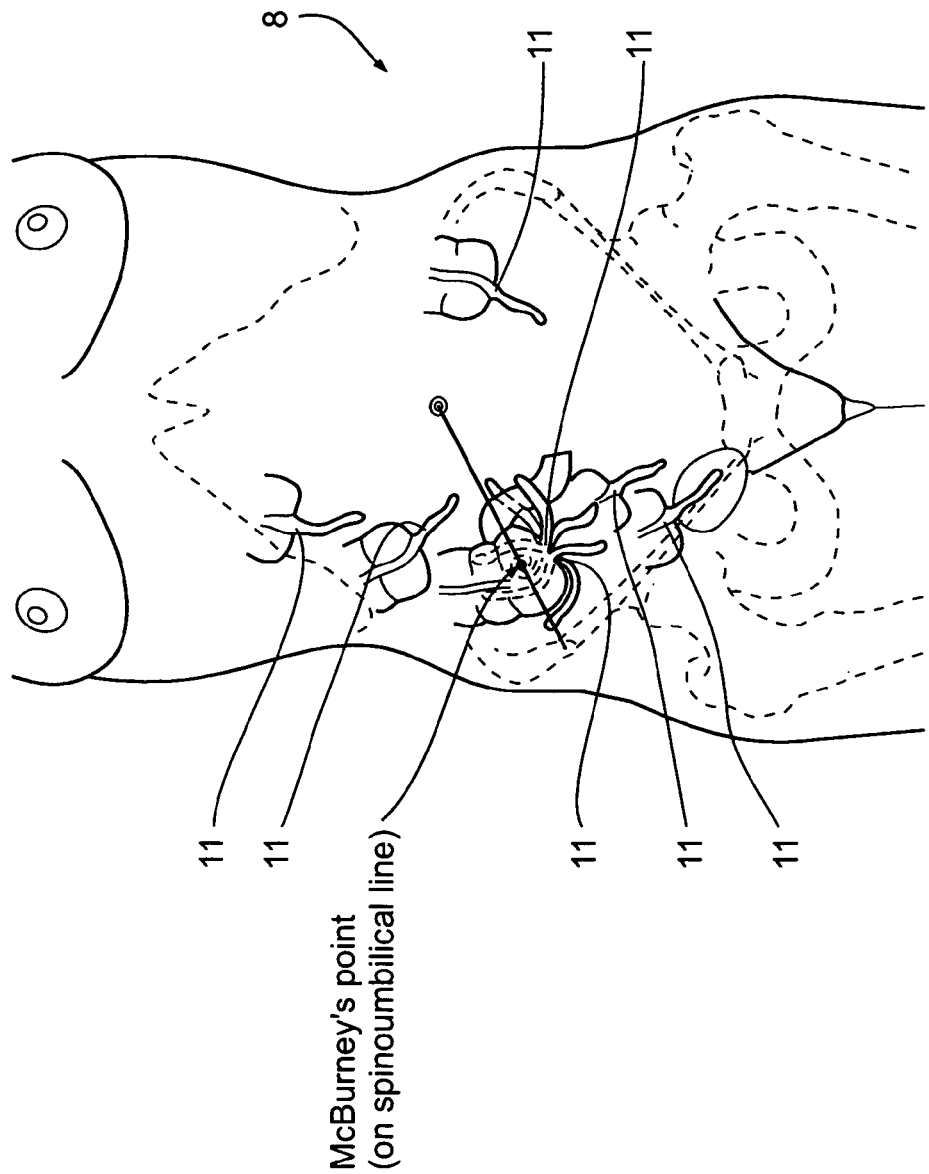

Referring now to the drawings, FIGS. 1A-1C schematically illustrate the gastrointestinal tract of a stomach 8, as follows:

FIG. 1A provides a general view of a small intestine 14, an ileum 5, a large intestine, or colon 16, and their junction 11 at a cecum 15.

FIG. 1B further illustrates colon 16, junction 11 between ileum 5 of small intestine 14 and cecum 15 of the colon, and an ileal orfice 13 between ileum 5 of small intestine 14 and cecum 15. Additionally, FIG. 1B illustrates a vermiform-appendix 17, a blind-ended tube connected to the caecum, which is often at a state of inflammation (Human appendix From the EvoWiki—www.evowiki.org.) It should be noted that vermiform appendix 17 may be observed by functional imaging, such as gamma or optical-fluorescence-spectroscopy imaging, designed to show the metabolic activity of body tissue, since inflamed and healthy tissues absorb pharmaceuticals at different rates.

An important feature of colon 16 is its semilunar folds 19, which provide it with a periodic structure, and which may be observed visually and by structural imaging such as ultrasound or MRI.

Colon 16 leads to a rectum 12 and to an external anal sphincter muscle 18, through which matter is eliminated from the body.

As seen in FIGS. 1A-1B, the diameter of colon 16 is about 2.5 times greater than the diameter of small intestine 14. Thus, an ingestible pill, sized to navigate its way along small intestine 14 and image its walls will be too small to properly image the walls of colon 16.

FIG. 1C illustrates variations in the position of junction 11 and appendix 17, within stomach 8, due both to peristaltic and to differences among individuals. As seen from FIG. 1C, it is not possible to define a fixed location within stomach 8 for junction 11, in relations to a fixed reference system of the body, for example, a pelvic bone 6. (FIG. 1C).

Table 1 [Encyclopedia of Controlled: Drug Delivery, volume 2, edited by Edith Mathiowitz] summarizes parameters of the gastrointestinal route, as relating to, liquid secretion and pH values.

TABLE 1

| SECTION | AREA, $M^2$ | LIQUID SECRETION, LITER/DAY | PH VALUE | TRANSIT TIME, HOUR |
|---|---|---|---|---|
| Oral cavity | ~0.05 | 0.5–2 | 5.2–6.8 | Short |
| Stomach | 0.1–0.2 | 2–4 | 1.2–3.5 | 1–2 |
| Duodenum | ~0.04 | 1–2 | 4.6–6.0 | 1–2 |
| Small Intestine | 4500 (including microvillies) | 0.2 | 4.7–6.5 | 1–10 |
| Large Intestine | 0.5–1 | ~0.2 | 7.5–8.0 | 4–20 |

As seen from Table 1, colon targeting may be based on pH value, since only in the colon the pH level is greater than 7. Other points worth noting are that the time an ingestible pill spends in the colon is considerable longer than that spent in any other portion of the gastrointestinal tract, yet the area to be imaged is orders of magnitude smaller than that of the small intestine. Additionally, secretion of gastrointestinal fluids in the colon is rather low.

Referring further to the drawings, FIGS. 2A-2B schematically illustrate an ingestible pill 10, navigating its way along small intestine 14 (FIG. 2A) and along colon 16 (FIG. 2B). A scale 4' schematically illustrates the difference in diameters between small intestine 14 and colon 16.

As seen in FIG. 2A, ingestible pill 10 is sized to navigate its way through and image the walls of small intestine 14, and thus makes good contact with the walls of small intestine 14. As: seen in FIG. 2B, in colon 16, ingestible pill-10 is too small and too far from the colon walls, to image them properly.

Referring further to the drawings FIGS. 3A-3B schematically illustrate an ideal situation, in which ingestible pill 10 expands in colon 16, to form expanded structure 10A (FIG. 3A), sized for good contact with the walls of colon 16, but contracts again to contracted ingestible pill 10B (FIG. 3B), on approaching external anal sphincter muscle 18, for elimination, in accordance with the present invention.

The expansion in colon 16, for better imaging of the colon walls, without interfering with pill elimination is the heart of the present invention, as illustrated in the Figures below.

Accordingly, FIGS. 4A-4C schematically illustrate, in flowchart forms, operational steps, using ingestible pills, according to the present invention;

As seen in FIG. 4A, a method 100 for imaging includes the following steps:

in a box 102, ingestible pill 10 is orally administered;

in a box 104, ingestible pill 10 navigates its way along the gastrointestinal tract, and possibly also images the walls of small intestine 14;

in a box 106, ingestible pill 10 detects entry to colon 16;

in a box 108, ingestible pill 10 expands to better image the walls of colon 16; and in a box 110, ingestible pill 10 images the walls of colon 16.

A method 105 for elimination includes the following steps:

in a box 114, external anal sphincter muscle 18 is detected;

in a box 116, ingestible pill 10 may contract on approaching external anal sphincter muscle 18, in preparation for elimination; and in a box 118, ingestible pill 10 is eliminated.

As seen in FIG. 4B, a method 105 for elimination includes the following steps:

in a box 114, external anal sphincter muscle 18 is detected;

in a box 116, ingestible pill 10 may contract on approaching external anal sphincter muscle 18, in preparation for elimination; and in a box 118, ingestible pill 10 is eliminated;

Alternatively, as seen in FIG. 4C, a method 115 for elimination includes the following steps:

in a box 113, ingestible pill 10, may be reshaped by pressure of external anal sphincter muscle 18, in preparation for elimination; and in a box 117, ingestible pill 10 is eliminated.

Figure 5I:
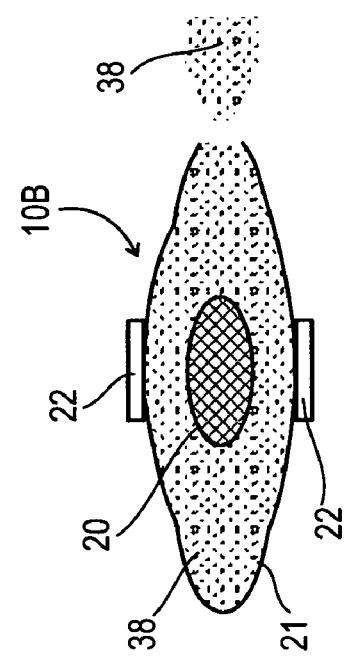
FIGS. 5A-5U schematically illustrate constructions of ingestible pills, adapted for expansion and possibly also contraction, in accordance with the present invention.
Figure 5H:
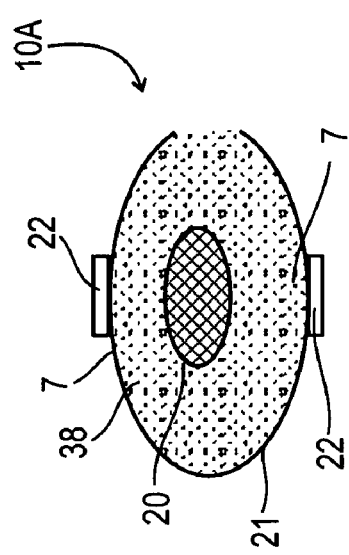
Figure 5G:
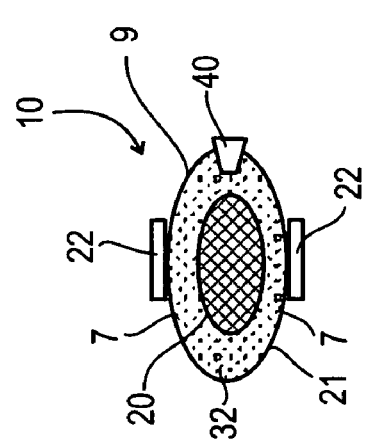
Figure 5L:
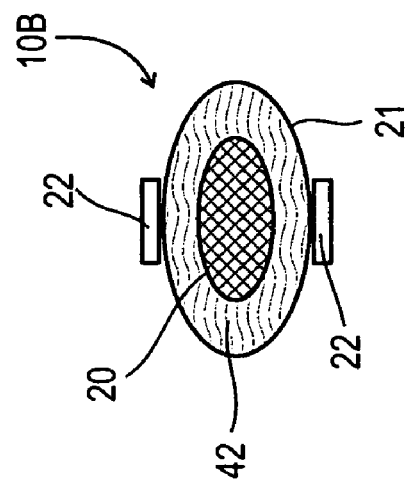
Figure 5K:
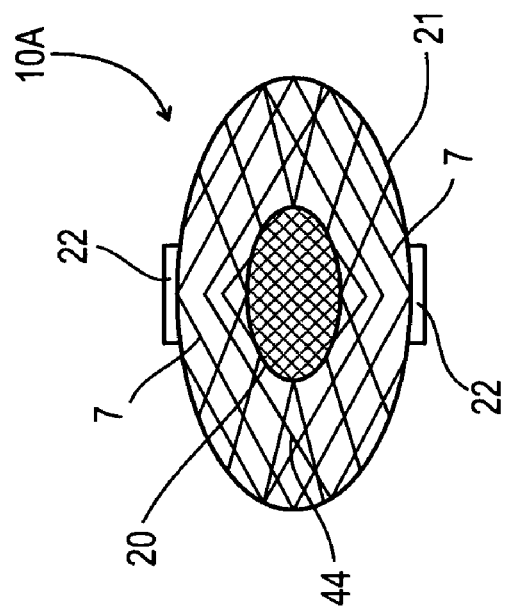
Figure 5J:
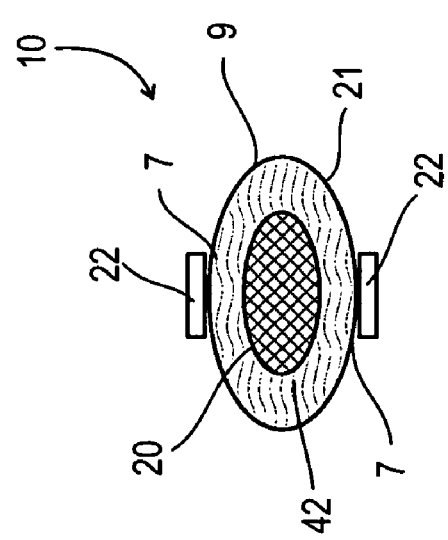
Figure 5N:
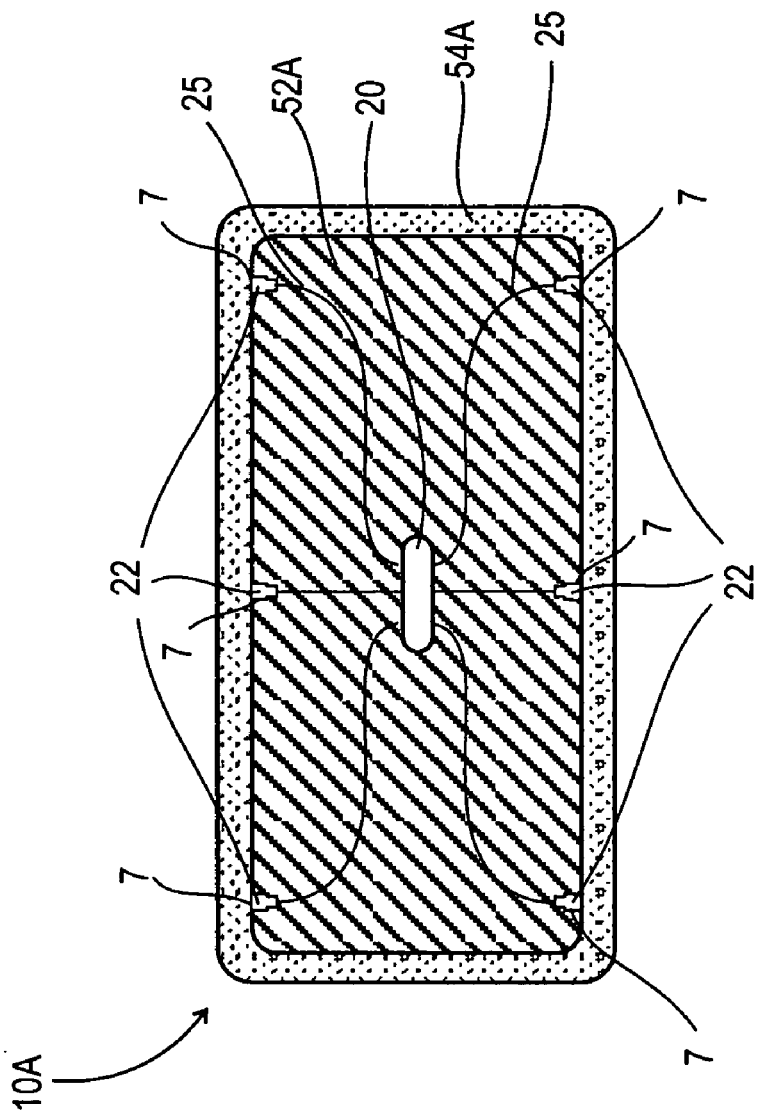
Figure 5M:
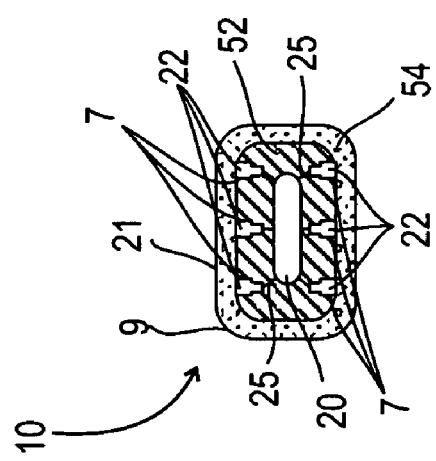
Figure 5S:
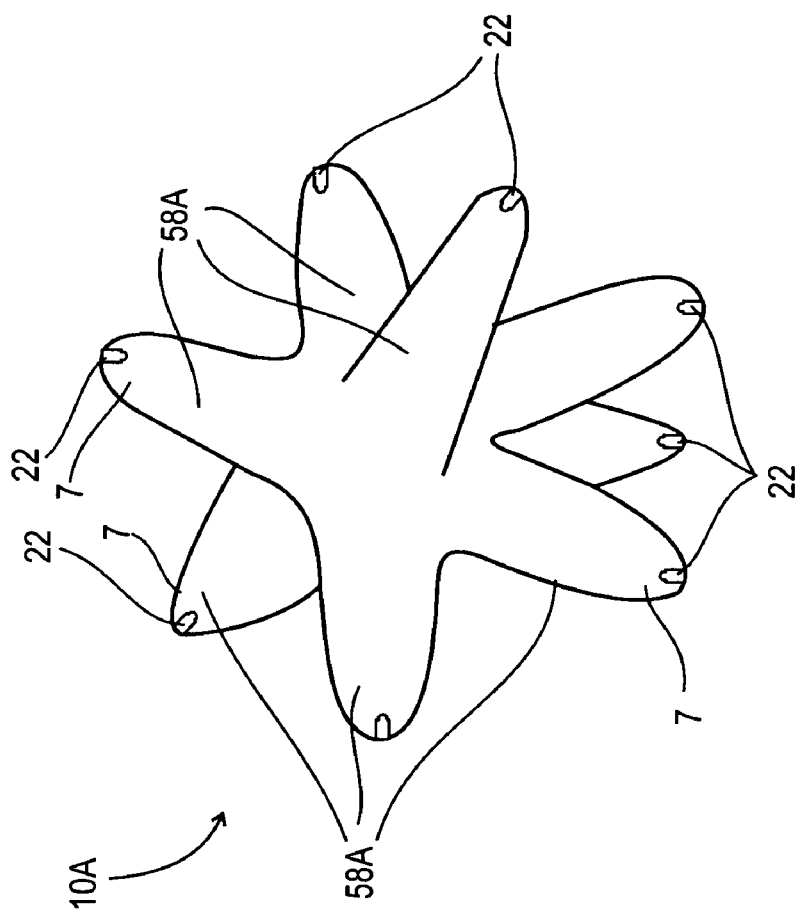
Figure 5R:
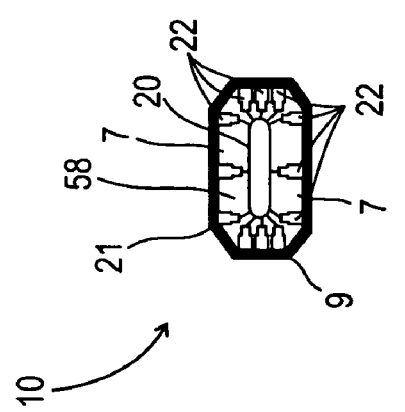
Figure 5U:
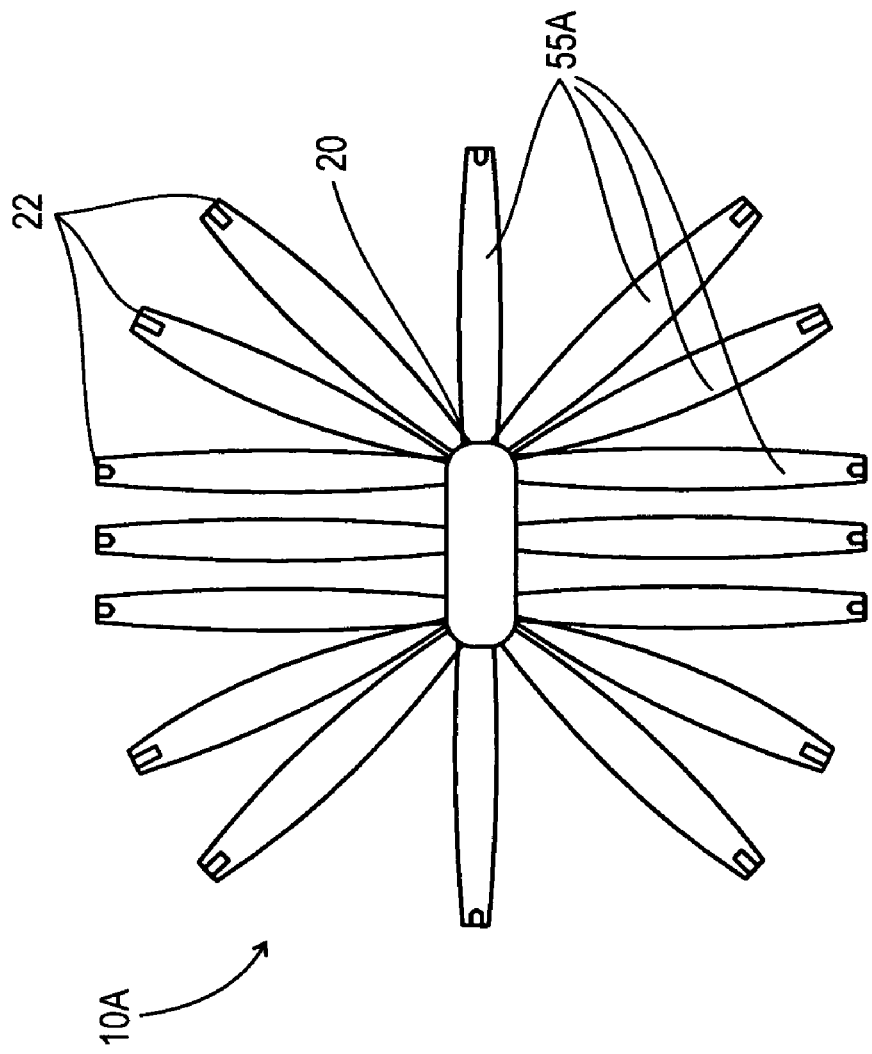

Referring further to the drawings, FIGS. 5A-5U schematically illustrate constructions of ingestible pills 10, adapted for expansion and possibly also contraction, in accordance with the present invention.

FIGS. 5A-5C illustrate a first embodiment of the present invention. Accordingly, in its contracted form (FIG. 5A), ingestible pill 10 has a volume 9, formed by a skin 21 and adapted for swallowing and for traveling within the gastrointestinal tract. Ingestible pill 10 further includes a core 20, containing the necessary electronic components, and one, two, or more detecting and (or) imaging probes 22, in an external region 7 near skin 21.

As used herein, detecting relates to performing instantaneous sensing, which may provide a "Yes" or "No" answer to the question, "Is there a suspicious finding?"Imaging, on the other hand, relates to constructing an image in a space, which may be one two or three dimensional. Where desired, instantaneous images may be stored as functions of time to further construct a "movie."

Preferably, detecting is performed first, for example, as part of screening or regular checkup procedures, and imaging is performed as a follow-up, when the detection results call for it.

Probes 22 may be connected to core 20 via cables 25, which are preferably wound or coiled, to allow for expansion. Additionally, skin 21 is preferably formed of an expansible material such as natural or synthetic rubber, or the like.

A space between core 20 and skin 21 includes two materials 26 and 28, separated by a diaphragm 23 having an electronically controlled valve 24.

Probes 22 and core 20 are adapted to provide an electronic signal, upon entering the colon, as will be described hereinbelow, in conjunction with FIGS. 6A-6B and 7A. Additionally, valve 24 is designed to open, responsive to the electronic signal, allowing materials-26 and 28 to mix or react.

When they mix or react, materials 26 and 28 expand into a material 30. The expansion may be the result of a gaseous production, for example, of $CO_2$, or of a production of a polymeric foam. As a consequence, an expanded structure 10A is formed. Skin 21 is stretched, and probes 22 are brought closer to the colon walls, for better imaging. Cables 25, which may be wound in FIG. 5A may be nearly taut in FIG. 5B.

Preferably, ingestible pill 10 has a length dimension L1 of about 30 mm and a width dimension D1 of about 15 mm. Preferably, the expansion is by a factor of between 3 and 4. Thus, after expansion, expanded structure 10A has a length dimension L2 of about 90-120 mm and a width dimension D2 of about 45-60 mm. It will be appreciated that other factors of expansion and other dimensions, both larger and smaller, are similarly possible, and are within the scope of the present invention. It will be further appreciated that for veterinary uses, different dimensions will be employed, applicable for a particular animal.

The embodiment of FIGS. 5A-5C illustrates an expanded structure 10A which may be squashed by the pressure of external anal sphincter muscle 18, into a longer and narrower shape 10B, for elimination, as illustrated in FIG. 4C, hereinabove.

FIGS. 5D-5F illustrate a second embodiment of the present invention. Accordingly, in its contracted form (FIG. 5D), ingestible pill 10 includes volume 9, formed by skin 21 and adapted for swallowing and for traveling within the gastrointestinal tract. Ingestible pill 10 further includes core 20, containing the necessary electronic components, and one, two, or more detecting and (or) imaging probes 22, in external region 7 near skin 21. Probes 22 are connected to core 20 via cables 25. The space between core 20 and skin 21 contains a material 32, adapted for expansion by osmosis, upon absorption of gastrointestinal fluids. Material 32 may be for example, a polyacrylic acid in a powder or cake form, a hydrogel, or guar gum. Other examples may include hydroxypropylmethylcellulose-HPMC or POLYOX™, which expand when in contact with water, and Laminaria digitata or Laminaria japonica, made from the root of a seaweed. Alternatively, SUPERABSORBNET, a powder that absorbs liquids and with the right mix with Gels Amilans can be form a sponge, or other super absorbent polymers, such as AQUA KEEP, may be used.

A first electronically controlled valve 34, being a one-way valve, allowing inflow only, is designed to open upon reaching the colon, as will be described hereinbelow, in conjunction with FIGS. 6A-6B and 7A. As a consequence, gastrointestinal fluids flow in, and material 32 expands by osmosis into a material 38, bringing imagers 32 closer to the colon walls.

A second electronically controlled valve 36 is designed to open on approaching external anal sphincter muscle 18, in preparation for elimination as illustrated in FIG. 4B, hereinabove, and as is further described hereinbelow, in conjunction with FIGS. 6A-6B and 7C. As a consequence, material 38 issues out of the ingestible pill, allowing it to return to a contracted form 10B.

Alternatively, second electronically controlled valve 36 is not used. Rather skin 21 may include one or more weak points 37, which may break or puncture under pressure allowing some of material 38 to issue out of the ingestible pill under the pressure of external anal sphincter muscle 18.

In accordance with an embodiment of the invention, skin, 21 is formed of a material, which deteriorates after about 20-25 hours in the colon environment, as a safety feature. Thus, if after 25 hours, expanded structure 10A has not been eliminated, skin 21 will deteriorate allowing material 38 to escape by outward diffusion.

FIGS. 5G-5I illustrate a third embodiment of the present invention. Accordingly, in its contracted form (FIG. 5G), ingestible pill 10 includes volume 9, formed by skin 21 and adapted for swallowing and for traveling within the gastrointestinal tract. Ingestible pill 10 further includes core 20, containing the necessary electronic components, and one, two, or more detecting and (or) imaging probes 22, in external region 7 near skin 21. Probes 22 are connected to core 20 via cables 25. The space between core 20 and skin 21 contains material 32, adapted for expansion, for example, by osmosis, upon absorption of water or gastrointestinal fluids. Material 32 may be, for example, polyacrylic acid in a powder or cake form. Alternatively another material which may absorb water or gastrointestinal fluids and expand may be used, for example, a hydrogel, guar gum, hydroxypropylmethylcellulose-HPMC, POLYOX™, Laminaria digitata, or Laminaria japonica.

Additionally, ingestible pill 10 includes a passive valve 40, formed of a material which dissolves in an environment of pH greater than 7, such as the colon environment. Thus, passive valve 40 is designed to: dissolve in the colon, and material 32 expands by osmosis to material 38, causing ingestible pill 10 to expand to expanded-structure 10A.

FIG. 5I illustrates natural elimination of squashed form 10B, since the hydrogel may be soft and pliable enough to yield under the pressure of external anal sphincter muscle 18. Additionally some material 38 may issue out since ingestible pill 10B has an open end, where dissolved plug 40 was.

FIGS. 5J-5L illustrate a fourth embodiment of the present invention. Accordingly, in its contracted form (FIG. 5J), ingestible pill 10 includes volume 9, formed by skin 21 and adapted for swallowing and for traveling within the gastrointestinal tract. Ingestible pill 10 further includes core 20, containing the necessary electronic components, and one, two, or more detecting and (or) imaging probes 22, in, external region 7 near skin 21. Probes 22 are connected to core 20 via cables 25.

Expansion takes place by a mechanical, stent-like device, whose expansion and contraction may be controlled by a miniature motor. Accordingly, FIGS. 5J and 5L illustrate a stent-like device 42 in its contracted state, and FIG. 5K illustrates deployed state 44.

Motor controlled expansion and contraction may be similar, for example, to the expansion and contraction of a car Jack, by the rotation of a controlling handle.

FIGS. 5M-5N illustrate a fifth embodiment of the present invention; wherein expansions takes place by two mechanism's. Accordingly, in its contracted form (FIG. 5M) ingestible pill 10 includes volume 9, formed by skin 21 and adapted for swallowing and for traveling within the gatrointestinal tract. Ingestible pill 10 further includes core 20, containing the necessary electronic components, and one, two, or more detecting and (or) imaging probes, 22, in external region 7 near skin 21. Probes 22 are connected to core 20 via cables 25.

Ingestible pill 10 is formed of a first material 52, adapted for osmosis expansion to form first expanded material 52A, (FIG. 5N); First material 52 is enclosed within a second material 54, adapted for expansion by water absorption to form expanded second material 54A.

First material 52 may be a powder or a cake, for example, of polyacrylic acid.

Second material 54 may be a pressed polymeric foam, such as a sponge, which expands as it fills with gastrointestinal fluids, upon exposure to them, while allowing gastrointestinal fluids to pass through it. At the same time, expanded second material 54A is adapted to enclose and contain first expanded material 52A, and provide it with a shape. Alternatively, a guar gum or a hydrogel, which absorb water, may be used, for second material 54.

As seen in FIG. 5M, skin 21, formed for example, as a coating, adapted to withstand the acidic environment of the stomach and small intestine, encapsulates ingestible pill 10. Skin 21 is designed to dissolve in the colon, for example, by enzymes or by a chemical reaction unique to the colon environment, allowing gastrointestinal fluids to reach first and second materials 52 and 54.

Preferably, expanded structure 10A is soft and pliable, having a consistency similar to a stool, allowing it to be naturally eliminated.

FIGS. 5O-5Q illustrate a sixth embodiment of the present invention Accordingly, in its contracted form (FIG. 5O) ingestible pill 10 includes volume 9, formed by skin 21 and adapted for swallowing and for traveling within the gastrointestinal tract. Ingestible pill 10 further includes core 20, containing the necessary electronic components, and one, two, or more detecting and (or) imaging probes 22, in external region 7 near skin 21. Probes 22 are connected to core 20 via cables 25.

Core 20 contains a pressurized or a liquefied gas balloon 55, for example, of $CO_2$, having an electronically controlled valve 53, which is in communication with a plurality of inflatable loops 56, adapted to expand to inflated loops 56A, for example, via inlet hoses 57. Each expanded loop 56A has a length dimension of about L2 and a width dimension, which is about half D2. The loops may issue from all sides of core 20, so as to form expanded structure 56A.

Probes 22 and core 20 are adapted to provide an electronic signal upon entering the colon, as will be described hereinbelow, in conjunction with FIGS. 6A-6B and 7A. Electronically controlled valve-53 is designed to open, responsive to the electronic signal.

As in the embodiment of FIGS. 5M-5N, skin 21 may be formed as a coating, which is adapted to withstand the acidic environment of the stomach and small intestine, and which is designed to dissolve in the colon, for example, by enzymes or by a chemical reaction unique to the colon environment.

Alternatively, skin 21 may be an stretchable layer, for example; of rubber, that expands with loops 56A and contains them therein.

Loops 56A are pliable and may be easily deformed for elimination.

FIGS. 5R-5S illustrate a seventh embodiment of the present invention. Accordingly, in its contracted form (FIG. 5R) ingestible pill 10 includes volume 9, formed by skin 21 and adapted for swallowing and for traveling within the gastrointestinal tract. Ingestible pill 10 further includes core 20, containing the necessary electronic components; and one, two, or more detecting and (or) imaging probes 22, in external region 7 near skin, 21. Probes 22 are connected to core 20 via cables 25.

In accordance with the present embodiment, ingestible pill 10 expands to form a star-fish-like expanded structure 10A. Star-fish-like expanded structure 10A may be inflatable, similar for example to the embodiment of FIGS. 5O-5Q, inflated by a gas balloon.

Alternatively, Star-fish-like expanded structure 10A may be a pressed foam, similar, to material 54 of FIGS. 5M-5N, and adapted to, expand by water absorption.

Skin 21 may be a coating, adapted to withstand the acidic environment of the stomach and small intestine, yet designed to dissolve in the colon, for example, by enzymes or by a chemical reaction unique to the colon environment.

Alternatively, where expanded structure 10A is inflated by gas, skin 21 may be stretched with it.

Figure 5T:
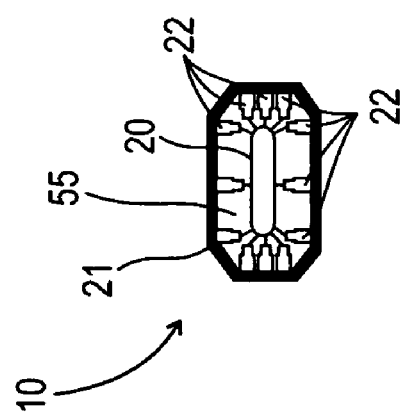

FIGS. 5T-5U illustrate an eighth embodiment of the present invention. Accordingly, in its contracted form (FIG. 5T) ingestible pill 10 includes volume 9; formed by skin 21 and adapted for swallowing and for traveling within the gastrointestinal tract. Ingestible pill 10 further includes core 20, containing the necessary electronic components, and one, two, or more detecting and, (or) imaging probes 22, in external region 7 near skin 21. Probes 22 are connected to core 20 via cables 25.

In accordance with the present embodiment, ingestible pill 10 expands to form a sea-urchin-like expanded structure 10A, having a plurality of flexible spines 55A. Sea-urchin-like expanded structure 10A may be inflatable, similar, for example, to the embodiment of FIGS. 5O-5Q, so as to be inflated by a gas balloon.

Alternatively, sea-urchin-like expanded structure 10A may be a pressed foam similar, to material 54 of FIGS. 5M-5N, and adapted to expand by water absorption.

Skin 21 may be a coating, adapted to withstand the acidic environment of the stomach and small intestine, yet designed to dissolve in the colon, for example, by enzymes or by a chemical reaction unique to the colon environment.

It will be appreciated that many other forms of expansion and contraction may be possible, and are within the scope of the present invention.

Figure 6A:
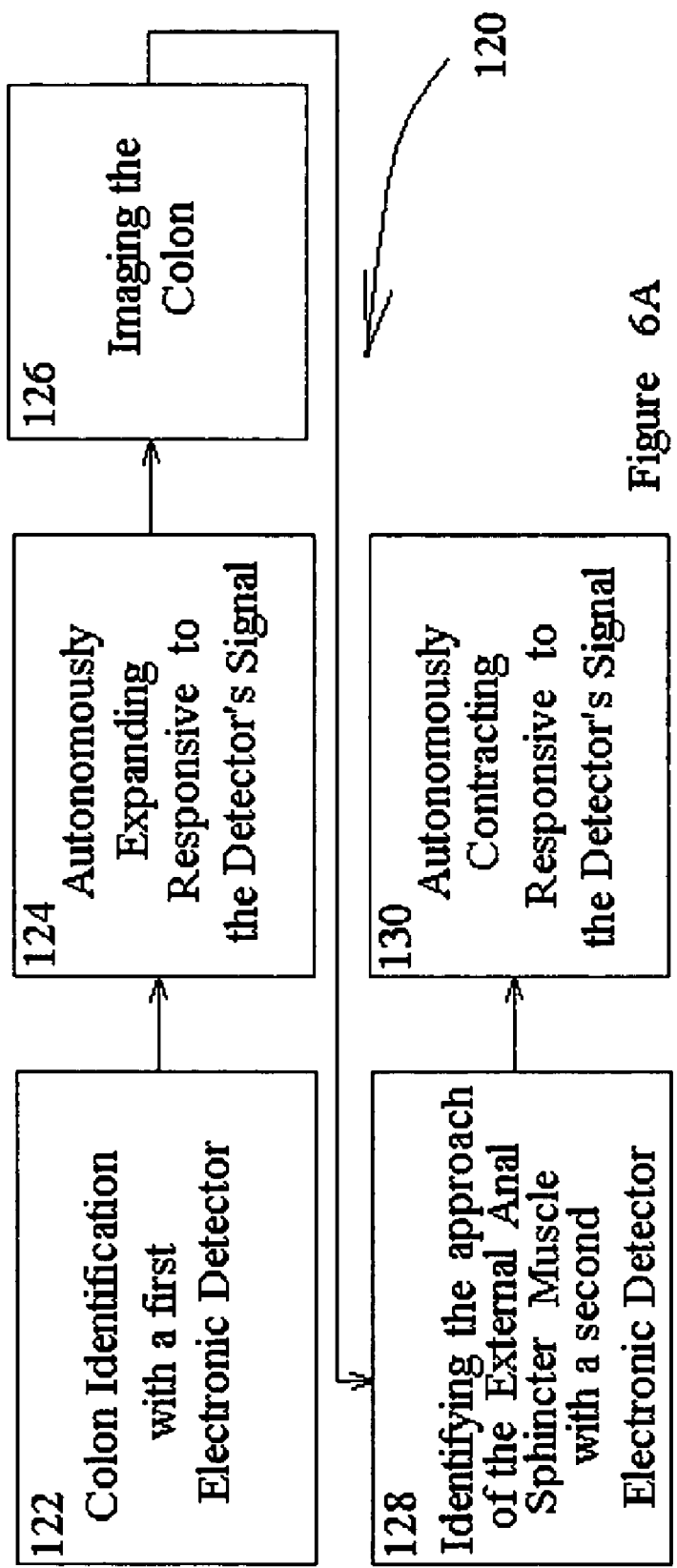
FIGS. 6A-6C schematically illustrate several methods for controlling the expansion and contraction of ingestible pills, in accordance with the present invention.
Figure 6B:
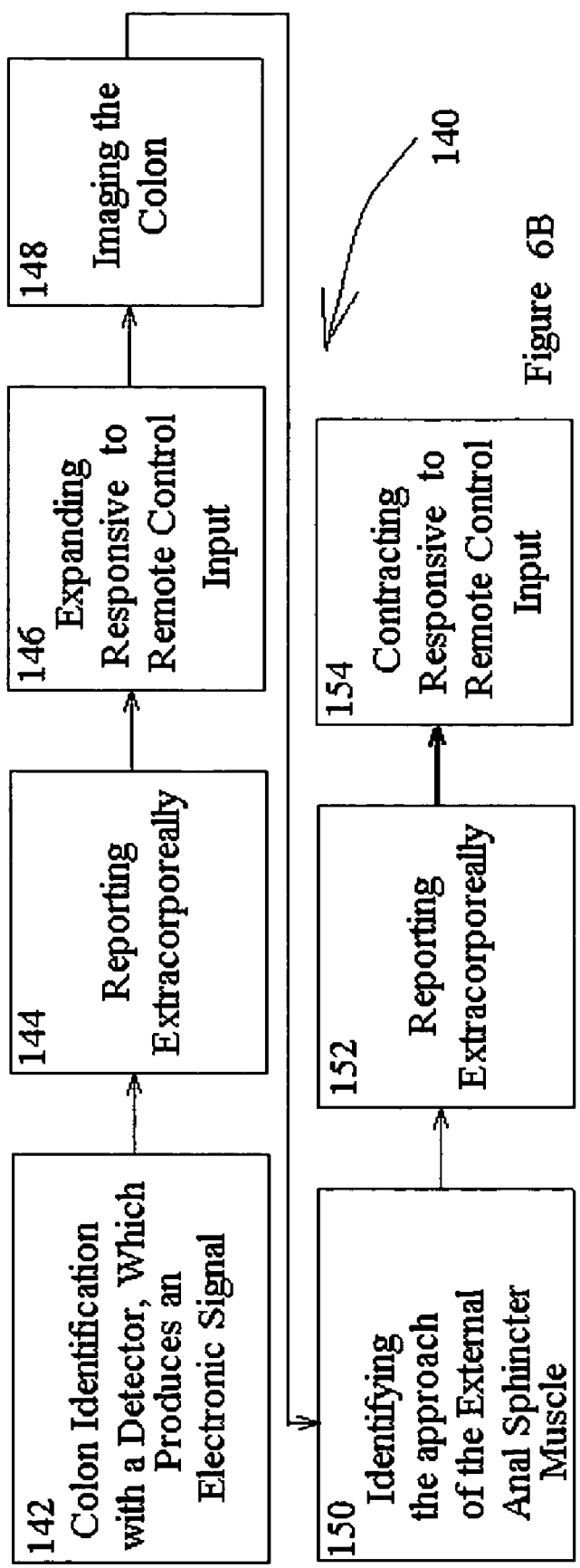
Figure 6C:
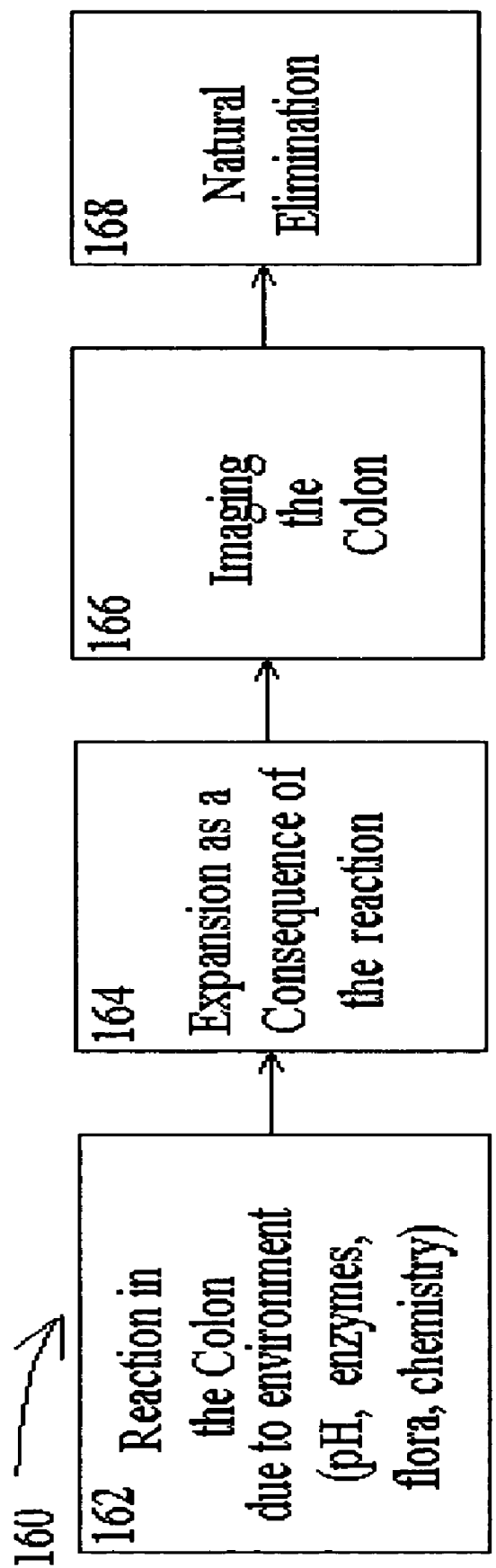
Figure 7A:
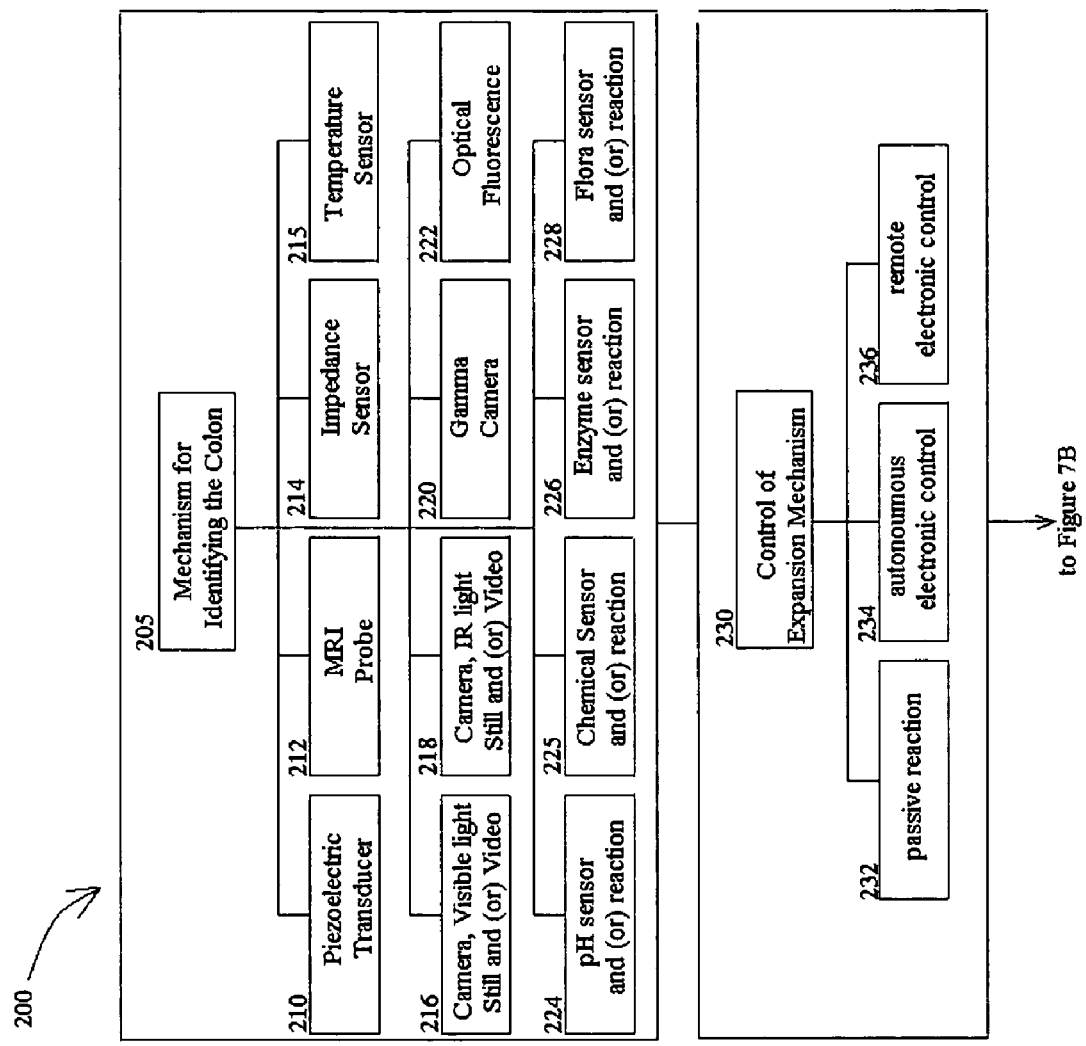
FIGS. 7A-7C schematically illustrate a summary flowchart of methods for colon identification, ingestible-pill expansion control, ingestible-pill expansion, ingestible-pill imaging, ingestible-pill contraction control, ingestible pill contraction or squashing, and ingestible-pill elimination, in accordance with the present invention.

Referring further to the drawings, FIGS. 6A-6C schematically illustrate several methods for controlling the expansion and contraction of ingestible pill 10, in accordance with the present invention.

FIG. 6A schematically illustrates an autonomous method 120, as follows:

in a box 122, colon identification takes place by a first detector which produces a first electronic signal, when entering the colon;

in a box 124, ingestible pill 10 expands autonomously, to expanded structure 10A responsive to the first electronic signal;

in a box 126, colon imaging takes place, by expanded structure 10A;

in a box 128, the external anal sphincter muscle 18 is identified using a second detector which produces a second electronic signal; and in a box 130, expanded structure 10A contracts autonomously, to ingestible pill 10B responsive to the second electronic signal.

Alternatively, FIG. 6B schematically illustrates an extracorporeally controlled method 140, as follows:

in a box 142, colon identification takes place by a first detector which produces a first-electronic signal, when entering the colon;

in a box 144, the first electronic signal is reported extracorporeally, in a box 146, ingestible pill 10 expands to expanded structure 10A responsive to a remote control input;

in a box 148, colon imaging takes place, by expanded structure 10A;

in a box 150, the external anal sphincter muscle 18 is identified using a second detector which produces a second electronic signal;

in a box 152, the second signal is reported extracorporeally; and in a box 154, expanded structure 10A contracts to ingestible pill 10B responsive to a remote control input.

Alternatively, FIG. 6C schematically illustrates a passive method 160, as follows:

in a box 162, a reaction, designed to occur at the colon's environment, based on the colon's pH, enzymes, flora (and) or chemistry, occurs in the colon;

in a box 164 expansion occurs as a consequence of the reaction, to form a soft, pliable expanded structure 10A;

in a box 166, colon imaging takes place, by expanded structure 10A; and in a box 168, natural elimination occurs.

It will be further appreciated that many combinations of these methods may be possible and are within the scope of the present invention.

Figure 7B:
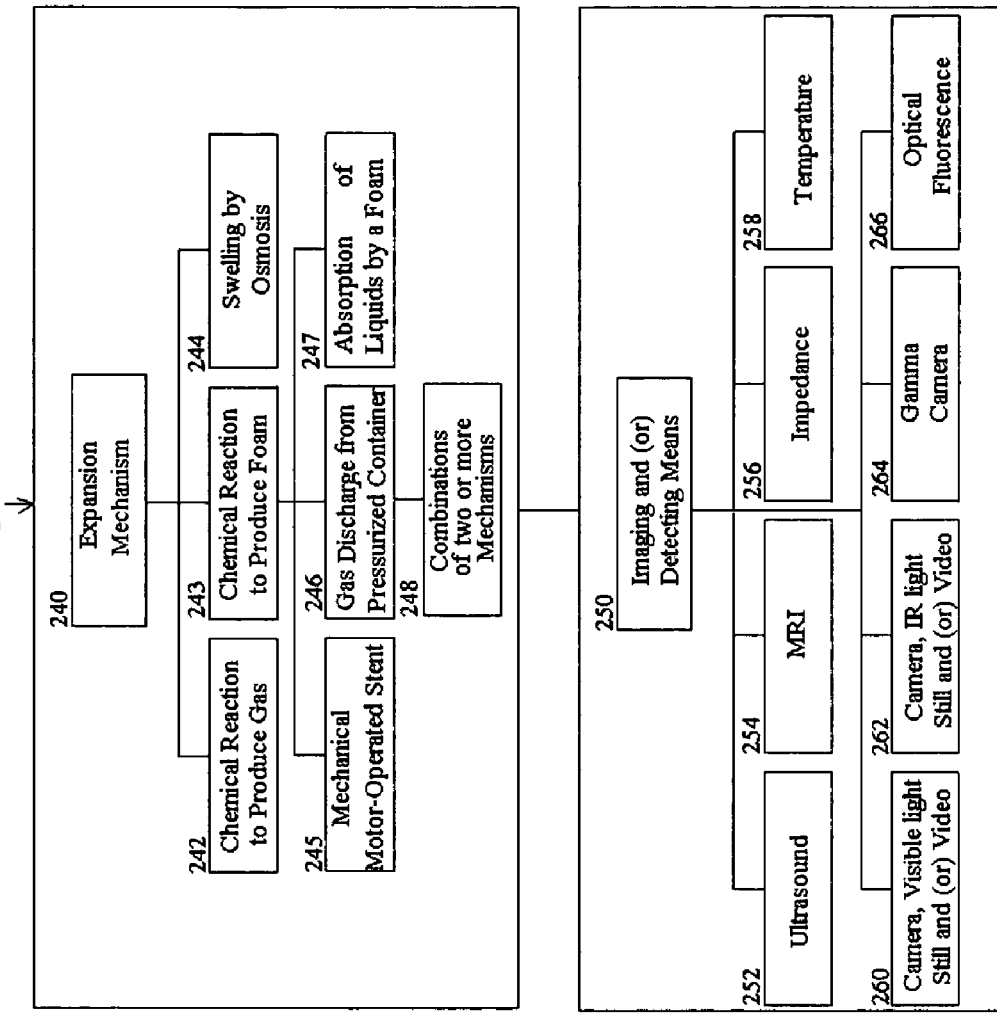
Figure 7C:
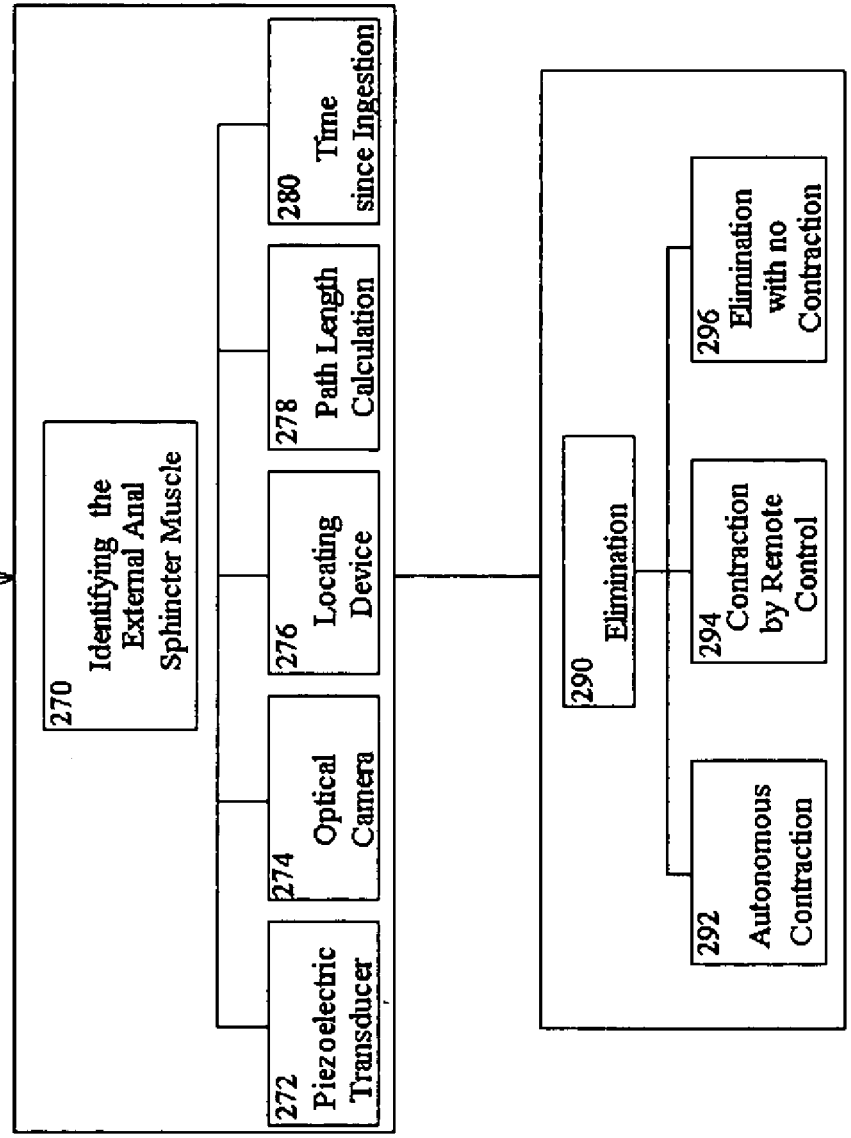

Referring further to the drawings; FIGS. 7A-7C schematically illustrates a summary flowchart 200 of methods for colon identification, ingestible-pill expansion control, ingestible-pill expansion, ingestible-pill imaging, ingestible-pill contraction control, ingestible pill contraction or squashing, and ingestible-pill elimination, in accordance with the present invention. Accordingly, A. In a box 205, colon identification may take place by any one of or a combination of the following:
  I. In a box 210, a piezoelectric transducer, based on any one of or a combination of the following:
    i. differences in ultrasound echo between small intestine 14 and colon 16;
    ii. a sudden change in ultrasound echo during the passage through ileal orfice 13 from ileum 5 of small intestine 14 to cecum 15; and (or)
    iii. the periodic echo of semilunar folds 19.
  II In a box 212, an MRI probes, based on-any one of or a combination of the following:
    i. differences in MRI images between small intestine 14 and colon 16;
    ii. a sudden change in MRI-images during the passage through ileal orfice 13 from ileum 5 of small intestine 14 to cecum 15; and (or)
    iii. the periodic effect of semilunar folds 19.
  III. In a box 214, electrodes for impedance measurements, based on differences in impedance measurements, upon entering the colon, between small intestine 14, with whose walls ingestible pill 10 makes general contact, and colon 16, with whose walls ingestible pill 10 makes little contact.

IV. In a box 215, by a temperature sensor, based on:
  i. differences in temperature between small intestine 14 and colon 16; and (or)
  ii. a hot spot near vermiform appendix 17 due to its general, inflammatory state.
V. In a box 216, a camera, which may be a video camera or a still camera; operable With visible light, based on any one of or a combination of the following:
  i. differences in visual effects between small intestine 14 and colon 16;
  ii. a sudden change in visual effects during the passage through ileal orfice 13 from ileum 5 of small intestine 14 to cecum 15, and (or)
  iii. visual effects of semilunar folds 19.
VI. In a box 218, a camera, which may be a video camera or a still camera, operable with infrared light, based on any one of or a combination of the following:
  i. differences in infrared visual effects between small intestine 14 and colon 16;
  ii. a sudden change in infrared visual effects during the passage through ileal orfice 13 from ileum 5 of small intestine 14 to cecum 15;
  iii. infrared visual effects of semilunar folds 19; and (or)
  iv. a hot spot near vermiform appendix 17 due to its general, inflammatory state.
VII. In a box 220, a gamma camera, based on a recognition of vermiform appendix 17, due to its general, inflammatory state.
VIII. In a box 222, optical-fluorescence-spectroscopy imaging, based on a recognition of vermiform appendix 17, due to its general, inflammatory state.
IX. In a box 224, a pH sensor or a pH controlled reaction, based on differences in pH value between small intestine 14 and colon 16.
X. In a box 225, a chemical sensor, based on differences in chemistry between small intestine 14 and colon 16. For example, in the colon, potassium is normally secreted into the lumen and complex sugars are fermented by the bacteria, forming the short-chain fatty acids (SCFAs) butyrate, propionate and acetate, which may serve as indications of the colon environment.
XI. In a box 226, by an enzyme sensor, based on differences in enzymes between small intestine 14 and colon 16. For example, in the small intestine, the plasma membrane of the microvilli contains digestive enzymes such as aminopeptidases and disaccharidases, which are absent in the colon thus, their absence may serve as indications of the colon environment. Additionally, Rubinstein et al., (Rubinstein et al., "In Vitro Evaluation of Calcium Pectinate: A Potential Colon-Specific Drug Delivery Carrier,"Pharm. Res. 10: 258-263, 1993) report colon targeting using calcium pectinate (CaPec) conjugate drugs, based on degradation of CaPec by colon specific (i.e., microflora-specific) enzymes and a hydrophobic drug incorporated into the insoluble CaPec matrices. Furthermore, Larsen et al. (Larsen et al., 1991, Acta Pharm Nord. 3: 41-44), 1991, Acta Pharm; Nord. 3: 41-44 report enzyme mediated release of drug from dextrin-drug conjugates by microflora specific enzymes for colon targeting.
XII. In a box 228, by a flora sensor, based on differences in flora between small intestine 14 and colon 16. For example, the contents of the small intestine are generally sterile, whereas the large intestine nourishes a large population of bacteria, of which the most common species is *E. coli*. Thus, the presence of E. coli may serve as an indication of the colon environment.

B. In a box 230, ingestible pill expansion control may take place by any one of or a combination of the following:
  I. In a box 232, a passive reaction, caused by the colon's environment.
  II. In a box 234, autonomously.
  III. In a box 236, by remote control.
C. In a box 240, ingestible-pill expansion may take place by any one of or a combination of the following:
  I. In a box 242, by a chemical reaction between two substances, to produce a gas.
  II. In a box 243, by a chemical reaction between two substances, to produce a foam.
  III. In a box 244, by osmosis, absorbing gastrointestinal fluids and swelling.
  IV. In a box 245, by an expansible, stent-like device, which is preferably motor controlled.
  V. In a box 246, by gaseous discharge from a pressurized gas container.
  VI. In a box 247, by the expansion of a foam as it absorbs liquids.
  VII. In a box 248, by a combination of items I-VI.
D. In a box 250, imaging and (or) detecting may take place by any one of or a combination of the following:
  I. In a box 252, by an ultrasound transducer.
  II. In a box 254, by an MRI probe.
  III. In a box 256, by an impedance probe.
  IV. In a box 258, by a temperature sensor.
  V. In a box 260, by a camera which may be a video camera or a still camera, using visible light.
  VI. In a box 262, by a camera which may be a video camera or a still camera, using infrared light.
  VII. In a boxy 264, by a gamma camera.
  VIII. In a box 266, by optical-fluorescence-spectroscopy imaging.
E. In a box 270, identifying the approach of external anal sphincter muscle 18 may take place by any one of or a combination of the following:
  I. In a box 272, by a piezoelectric transducer, based on anyone of the following:
    i. increased pressure of external anal sphincter muscle 18; and (or)
    ii. absence of periodic ultrasound echo of Semilunar folds 19.
  II. In a box 274, by a camera, based on the absence of semilunar folds 19.
  III. In a box 276, by locating ingestible pill 10 near external anal sphincter muscle 18.
  IV. In a box 278, by calculating the path length traveled by ingestible pill 10 in colon 16.
  V. In a box 280, based on the time since ingestion.
F. In a box 290 ingestible pill elimination may take place by any one of or a combination of the following:
  I. In a box 292, autonomous contraction.
  II. In a box 294, contraction by remote control.
  III. In box 296, without contraction, when the expanded form is pliable and soft.

Detecting and Imaging Techniques

The ingestible pill, in accordance with the present invention, may be used as a mere detection tool, for first identification of pathologies, wherein after detection of a suspected pathology by the ingestible pill, a second apparatus, for example, a colonoscope equipped with a gamma probe may be used for extensive imaging.

Alternatively, the ingestible pill, in accordance with the present invention, may be used as an imaging apparatus.

The imaging and (or) detection techniques of the present invention may be as described in commonly owned U.S. Patent Application 20030139661, to Kimchy et al., entitled, "Ingestible pill," whose disclosure is incorporated herein by reference, and which describes an ingestible device, adapted to travel in the gastrointestinal tract and perform a diagnostic image of tissue therein. The diagnostic image may comprise diagnostic information as a function of time, or diagnostic information as a function of distance traveled within the gastrointestinal tract. Specifically, the ingestible device may be arranged to perform a diagnostic image of nuclear radiation of a radiopharmaceutical, scintillation of a scintillation liquid, responsive to nuclear radiation of a radiopharmaceutical, optical fluorescence of a fluorescing pharmaceutical or of bare gastrointestinal-tract tissue, infrared radiation of the gastrointestinal-tract tissue, temperature-differences along the gastrointestinal-tract, impedance, ultrasound reflection, magnetic resonance, and a combination thereof. The ingestible device may be adapted for general screening of a large population, on the one hand, and for the specific diagnoses of suspected pathologies, on the other.

Additionally, the imaging and (or) detection techniques of the present invention may be as described in commonly owned U.S. Patent Application 20040054278, to Kimchy, et al., entitled "Ingestible device" whose disclosure is incorporated herein by reference, and which relates to an ingestible pill, adapted to travel in the gastrointestinal tract and perform a diagnostic image of tissue therein. The diagnostic image may comprise diagnostic information as a function of time, or diagnostic information as a function of distance traveled within the gastrointestinal tract. An imaging method by depth calculations is provided, based on the attenuation of photons of different energies, which are emitted from the same source, coupled with position monitoring.

Additionally, the imaging and (or) detection techniques may be as follows:

Gamma Imaging and (or) Detection:

Gamma imaging and (or) detection may be performed, for example, using radiopharmacueticals such as monoclonal antibodies, such as CEA Scan (arcitumomab), made by Immunomedics Inc., or other agents, e.g., fibrinogen or fluorodeoxyglucose, tagged with a radioactive isotope, e.g., $^{99M}$technetium, $^{67}$gallium, $^{201}$thallium, $^{111}$indium, $^{123}$iodine, $^{125}$iodine and $^{18}$fluorine, which may be administered orally, intravenously, or even rectally.

Additionally, the gamma imager, or radioactive-emission probe may be constructed of room temperature CdZnTe, obtained, for example; from eV Products, a division of II-VI Corporation, Saxonburg Pa., 16056. Alternatively, another solid-state detector such as CdTe, HgI, Si, Ge, or the like, or a scintillation detector, such as NaI(T1), LSO, GSO, CsI, CaF, or the like, or another detector as known, may be used. The radioactive-emission probe may be a single-pixel or a multi-pixel probe. Preferably, each pixel is about 3 mm×3 mm in size.

It will be appreciated that other radioactive-emission probes, as known, may be used.

For example, the radioactive-emission probe may be constructed as taught by U.S. Pat. No. 4,782,840 to Martin, Jr., et al., entitled, "Method for locating, differentiating, and removing neoplasms," whose disclosure is incorporated herein by reference, or as taught by other works; which illustrate radioimmnunoguided surgery, or RIGS™. (RIGS is a registered trademark of Neoprobe Corporation of Dublin, Ohio).

Alternatively, radioactive-emission probe may be constructed as taught by U.S. Pat. No. 4,801,803 to Denen, et al., entitled, "Detector and localizer for low energy radiation emissions-" whose disclosure is incorporated herein by reference, and which describes a probe particularly suited for use in immuno-guided surgery capable of detecting, very faint gamma emissions and thereby localizing cancerous tumor. Detection is achieved under room temperature conditions using a crystal such as cadmium telluride. To achieve the extreme sensitivity capabilities of the apparatus, an instrumentation approach has been developed in which the somewhat fragile crystal is securely retained in isolation, from externally induced incidents otherwise creating excessive noise. Microphonic effects are minimized through employment of a sequence of materials' exhibiting divergent acoustic impedance. Capacitive effects caused by minute intercomponent movements are controlled to acceptable levels.

Additionally, a preamplifier is incorporated within the probe itself, which employs an integrator stage front end combining a field effect transistor and bipolar device with a very small feedback capacitance of less than one picofarad. A bootstrap technique is utilized to enhance the amplification of the bipolar amplification stage. Pulse related signals outputted from the device are normalized and compared to produce pulse data, which ate analyzed. In one mode of operation a siren effect is employed to guide the surgeon towards emission sources.

The aforementioned probe is directed at low energy radionucleides, such as $I^{125}$. Additionally, the distribution of radiolabeled antibody with the nuclide is quite sparse so that background emissions can be minimized and the ratio of tumor-specific counts received to background counts can be maximized. The probe instrument and related control circuitry has been assigned the trade designation "NEOPROBE" instrument.

Alternatively, radioactive-emission probe may be constructed as taught by U.S. Pat. Nos. 5,151,598, or 5,070,878, or 4,893,013, all to Denen, and all entitled, "Detector and localizer for low energy radiation emissions," all of whose disclosures are incorporated herein by reference. Alternatively, radioactive-emission probe may be constructed as taught by U.S. Pat. No. 6,259,095, to Boutun, et al., entitled, "System and apparatus for detecting and locating sources of radiation," whose disclosure is incorporated herein by reference.

Optical-Fluorescence-Spectroscopy Imaging and (or) Detection:

Optical-fluorescence-spectroscopy imaging and (or) detection may be performed, for example, using fluorescence pharmaceuticals. For example, ematoporphyrin derivatives (HPD), give a well-structured fluorescence spectrum, when excited in the Soret band around 405 nm. The fluorescence spectrum shows typical peaks at about 630 and 690 nm, superimposed in practice on more unstructured tissue autofluorescence. Other useful tumor-marking agents are dihematoporphyrin ether/ester (DHE), hematoporphyrin (HP), polyhematoporphyrin ester (PHE), and tetrasulfonated phthalocyanine. (TSPC), when irradiated at 337 mm ($N_2$ laser), and any other fluorescence- or Rhodamine-based dyes. These may be administered orally, intravenously, or rectally.

Additionally, the optical fluorescence probe may be constructed as taught by U.S. Pat. No. 5,115,137, to Andersson-Engels, et al, entitled, "Diagnosis by means of fluorescent light emission from tissue," whose disclosure is incorporated herein by reference, and which relates to improved detection of properties of tissue by means of induced fluorescence of large molecules. The tissue character may then be evaluated from the observed large-molecule spectra. According to U.S.

Pat. No. 5,115,137, the spectrum for tonsil cancer is clearly different from normal mucosa, due to endogenous porphyrins.

Alternatively, the optical fluorescence probe may be constructed as taught by U.S. Pat. No. 4,785,806, to Deckelbaum, entitled, "Laser ablation process and apparatus," whose disclosure is incorporated herein by reference and which describes a process and apparatus for ablating atherosclerotic or neoplastic tissues. Optical fibers direct low power light energy at a section of tissue to be ablated to cause the section to fluoresce. The fluorescence pattern is analyzed to determine whether the fluorescence frequency spectrum is representative of normal or abnormal tissue. A source of high power, ultraviolet, laser energy directed through an optical fiber at the section of tissue is fired only when the fluorometric analysis indicates that it is directed at abnormal tissue.

Alternatively, the optical fluorescence probe may be constructed as taught by U.S. Pat. No. 4,682,594, to Mok, entitled, "Probe-and fire lasers,"whose disclosure is incorporated herein by reference, and which describes a method and apparatus of irradiating a treatment area within a body, such as blood vessel plaque.

Alternatively, the optical fluorescence probe may be constructed as taught by U.S. Pat. No. 4,336,809 to Clark, entitled, "Human and animal tissue photoradiation system and method," whose disclosure is incorporated herein by reference. It relates to utilizing certain dyes, which not only selectively stain neoplastic tissue but also fluoresce in response to irradiation. Additionally, they are photodynamically cytotoxic in response to a proper wavelength of light in the presence of oxygen within living tissue. One of the dyes that is presently preferred for these characteristics contains hematoporphyrin or hematoporphyrin derivatives that when administered intravenously remain at higher concentrations for longer periods of time in traumatized or malignant tumorous tissue than in normal tissue. This dye also has a strong absorption peak centered at a wavelength of approximately 407 nanometers and responds to excitation at about this wavelength by fluorescing at a wavelength of about 614 nanometers. This makes tumor diagnosis possible by injecting the dye, allowing it to concentrate in tumorous tissue, irradiating the tissue with deep blue violet light, and observing red fluorescence. Thus, the difference in the optical property of the stained tissue and the unstained healthy tissue improves the visualization of the treatment area. This same dye has a photodynamic absorption peak at a wavelength of about 631 nanometers and is cytotoxic to malignant tissue, containing the dye when irradiated with red light of about this wavelength. For diagnostic purposes krypton ion laser was used for its 406.7/4113.1 nanometer lines matching the 407 nanometer absorption peak of hematoporphyrin.

Alternatively, the optical fluorescence probe may be constructed as taught by U.S. Pat. No. 6,258,576, to Richards-Kortum, et al., entitled, "Diagnostic method and apparatus for cervical squamous intraepithelial lesions in vitro and in vivo using fluorescence spectroscopy," whose disclosure is incorporated herein by reference, and which relates to the use of multiple illumination wavelengths in fluorescence spectroscopy for the diagnosis of cervical cancer and precancer. In this manner, it has been possible to (i) differentiate normal or inflamed tissue from squamous intraepithelial lesions (SILs) and (ii) differentiate high grade SILs from non-high grade SILs. The detection may be performed in vitro or in vivo. Multivariate statistical analysis has been employed to reduce the number of fluorescence excitation-emission wavelength pairs needed to re-develop algorithms that demonstrate a minimum decrease in classification accuracy.

Ultrasound Imaging and (or) Detection:

The ultrasound probe for imaging and (or) detection may be constructed, for example, as taught by U.S. Patent Application 20010020131, to Kawagishi, Tetsuya, et al., entitled, "Ultrasonic diagnosis system," whose disclosure is incorporated herein by reference, and which describes an ultrasonic diagnosis apparatus that has an ultrasonic probe, having a plurality of arrayed transducer elements, a transmitting beam former for generating driving, signals for driving transducer elements, and a receiving beam former for generating receiving signals based on echo signals received by transducer elements. The transmitting beam former generates driving signals so that phases of ultrasonic waves generated from transducer elements are aligned at multiple focal points. An image processor extracts harmonic components from receiving signals of ultrasonic waves having multiple focal points, and generates ultrasonic image data based on the harmonic components.

Alternatively, the ultrasound imager may be constructed, for example, as taught by, U.S. Pat. No. 5,284,147, to Hanoaka, et al., entitled, "Ultrasonic probe to be installed on fingertip," whose disclosure is incorporated herein by reference, and which relates to an ultrasonic probe to be inserted into the body of a subject for image-processing a diagnostic target thereof by ultrasonic waves transmitted to and received from the inside of the body.

Contrast agents may be used in conjunction with ultrasound imaging, for example as taught by U.S. Pat. No. 6,280,704, to Schutt, et al., entitled, "Ultrasonic imaging system utilizing a long-persistence contrast agent," whose disclosure is incorporated herein by reference.

MRI Imaging and (or) Detection:

The MRI probe for imaging and (or) detection may be constructed, for example, as taught by U.S. Pat. No. 5,572,132, to Pulyer, et al., entitled, "MRI probe for external imaging," whose disclosure is incorporated herein by reference, wherein an MRI catheter for endoscopical imaging of tissue of the artery wall, rectum, urinal tract, intestine, esophagus, nasal passages, vagina and other biomedical applications is described.

The invention teaches an MRI spectroscopic probe having an external background magnetic field $B_0$ (as opposed to the internal background magnetic filed of the large horizontal bore superconducting magnet.) The probe comprises (i) a miniature primary magnet having a longitudinal axis and an external surface extending in the axial direction and (ii) a RF coil surrounding and proximal to said surface. The primary magnet is structured and configured to provide a symmetrical, preferably cylindrically shaped, homogeneous field region external to the surface of the magnet. The RF coil receives NMR signals from excited nuclei. For imaging, one or more gradient coils are provided to spatially encode the nuclear spins of nuclei excited by an RF coil, which may be the same coil used for receiving NMR signals or another RF coil.

Preferably, for MRI imaging and (or) detection, contrast-agents, such as, which are preferably tied to antibodies, such as may be used.

Video Camera Imaging and (or) Detection:

The video camera may be constructed, for example, as taught by U.S. Pat. No. 5,604,531, to Iddan, et al., entitled, "In vivo video camera system," whose disclosure is incorporated herein by reference, describes a video camera system, encapsulated within an ingestible pill, arranged to pass through the entire digestive tract, operating as an autonomous video endoscope. The ingestible-pill includes a camera system and an optical system for imaging an area of interest onto the camera system, and a transmitter, which relays the video output of the camera system to an extracorporeal reception system. A light source is located within a borehole of the optical system.

Additionally, the light source may be visible light or infrared light.

Additionally or alternatively, the video camera may be constructed, for example, as taught by U.S. Patent Application 20010035902, to Iddan, G. J., et al., entitled, "Device and system for in vivo imaging," whose disclosure is incorporated herein by reference, and which describes a system and method for obtaining in vivo images. The system contains an imaging system and an ultra, low power radio frequency transmitter for transmitting signals from the CMOS imaging camera to a receiving system located outside a patient. The imaging system includes at least one CMOS imaging camera, at least one illumination source for illuminating an in vivo site and an optical system for imaging the in vivo site onto the CMOS imaging camera.

Camera Detection;

It will be appreciated that a simple camera may also be used, as a detection tool.

Temperature Imaging and (or) Detection:

The temperature sensor for imaging and (or) detection may be constructed, as an infrared thermography imager, taught by Harzbecker K, et al., "Thermographic thorax diagnostics," Z Gesamte Inn Med. 1978 Feb. 1;33(3):78-80, and by Dexter L I, Kondrat'ev VB., "Thermography in differential diagnosis of lymphostasis in the lower limbs," Vestn Khir Im I I Grek. 1976 June; 116(6):60-4.

Impedance Imaging and (or) Detection:

An Impedance probe for imaging and (or) detection may be constructed, for example, as taught by U.S. Pat. Nos. 6,308,097, 6,055,452 and 5,810,742, to Pearlman, A. L., entitled, "Tissue characterization based on impedance images and on impedance measurements," whose disclosures are incorporated herein by reference.

Alternatively, it may be constructed as taught by U.S. Pat. No. 4,458,694, to Sollish, et al., entitled, "Apparatus and method for detection of tumors in tissue," whose disclosure is incorporated herein by reference. For example, the impedance imager may include a probe, comprising a plurality of elements, means for applying an AC signal to the tissue; means for sensing electrical properties at each of the probe elements at different times, and signal processing circuitry, coupled to the sensing means, for comparing the electrical properties sensed at the different times. The impedance imager may thus provide an output of the dielectric constants of localized regions of tissue.

It will be appreciated that the present invention is applicable to humans and animals, taking into account the digestive system anatomy of each animal.

As used herein, the term about refers to ±20%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications in printed or electronic form, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An ingestible pill, adapted to recognize entry to a colon, comprising:

an ingestible-pill body, adapted to be swallowed by a living being and adapted for traveling down a gastrointestinal tract of the living being, the body including an expansion mechanism and an outer portion, wherein at least part of the outer portion is adapted to be moved by said expansion mechanism relative to an opposite part of the outer portion and wherein the part of the outer portion includes at least one radioactive-emission detector for detecting pathologies in the colon; and a colon-recognition trigger mechanism, associated with the ingestible-pill body and configured to produce a colon-entry signal, when the ingestible-pill body enters the colon of the living being, wherein the outer portion comprises a skin, and wherein the at least one radioactive-emission detector contacts the skin.

2. The ingestible pill of claim 1, wherein the colon-recognition trigger mechanism is selected from the group consisting of:

an ultrasound sensor, configured to produce the colon-entry signal, based on the difference in structure between the small intestine and the colon, an MRI sensor, configured to produce the colon-entry signal, based on the difference in structure between the small intestine and the colon, a video camera, configured to produce the colon-entry signal, based on the difference in structure between the small intestine and the colon, an ultrasound sensor, configured to produce the colon-entry signal, upon imaging the semilunar fold structure, which is unique to the colon, an MRI sensor, configured to produce the colon-entry signal, upon imaging the semilunar fold structure, which is unique to the colon, a video camera, configured to produce the colon-entry signal, upon imaging the semilunar fold structure, which is unique to the colon, a radioactive-emission sensor, configured to produce the colon-entry signal, upon functional sensing the generally inflammatory state of the vermiform appendix, an optical-fluorescence-spectroscopy sensor, configured to produce the colon-entry signal, upon functional sensing the generally inflammatory state of the vermiform appendix, a pH sensor, configured to produce the colon-entry signal, upon sensing the pH environment of the colon, which is greater than 7, an enzyme sensor, configured to produce the colon-entry signal, upon sensing the enzyme environment of the colon, a chemical sensor, configured to produce the colon-entry signal, upon sensing the chemical environment of the colon, a bacterial sensor, configured to produce the colon-entry signal, upon sensing the flora environment of the colon, and a combination of the above.

3. The ingestible pill of claim 1, wherein the expansion mechanism is configured to expand the ingestible pill body into an expanded structure, having expanded length and width parameters, which are between a factor of two and a factor of five greater than the initial length and width parameters, so as to push the outside portion in an outward direction from the center of the body, when the colon-recognition trigger mechanism produces the colon-entry signal.

4. The ingestible pill of claim 3, wherein the ingestible pill expands generally uniformly.

5. The ingestible pill of claim 3, wherein the expanded structure has a shape, selected from the group consisting of an elliptical capsule, a plurality of loops, a star fish, and a plurality of spines.

6. The ingestible pill of claim 1, wherein the expansion mechanism is an absorption mechanism, selected from the group consisting of the absorption of gastrointestinal fluids by osmosis, the absorption of gastrointestinal fluids by a foam, the absorption of gastrointestinal fluids by guar gum, the absorption of gastrointestinal fluids by polyacrylic acid, the absorption of gastrointestinal fluids by a hydrogel, the absorption of gastrointestinal fluids by hydroxypropylmethylcellulose-HPMC, the absorption of gastrointestinal fluids by polyethylene oxide, the absorption of gastrointestinal fluids by Laminaria digitata, the absorption of gastrointestinal fluids by Laminaria japonica, a combination of the above.

7. The ingestible pill of claim 1, wherein the colon-recognition trigger mechanism is further operative as a detector for detecting pathologies in the colon.

8. The ingestible pill of claim 7, and further including another detector for detecting pathologies in the colon, wherein the at least one radioactive-emission detector and the another detector are of the same type.

9. The ingestible pill of claim 7, and further including another detector for detecting pathologies in the colon, wherein the at least one radioactive-emission detector and the another detector are of different types.

10. The ingestible pill of claim 9, wherein the another detector for detecting pathologies in the colon is selected from the group consisting of at least one optical fluorescence sensor, at least one ultrasound sensor, at least one MRI sensor, at least one still camera operative in a visible light range, at least one video camera, operative in a visible light range, at least one still camera operative in an infrared light range, at least one video camera, operative in an infrared light range, at least one temperature sensor, and at least one impedance sensor.

11. The ingestible pill of claim 7, wherein the another detector for detecting pathologies in the colon is further configured as an imager, for imaging pathologies in the colon, as a function of position along the colon.

12. The ingestible pill of claim 1, and further including another detector for detecting pathologies in the colon, wherein the at least one radioactive-emission detector and the another detector are of the same type.

13. The ingestible pill of claim 1, and further including another detector for detecting pathologies in the colon, wherein the at least one radioactive-emission detector and the another detector are of different types.

14. The ingestible pill of claim 13, wherein the another detector for detecting pathologies in the colon is selected from the group consisting of at least one optical fluorescence sensor, at least one ultrasound sensor, at least one MRI sensor, at least one still camera operative in a visible light range, at least one video camera, operative in a visible light range, at least one still camera operative in an infrared light range, at least one video camera, operative in an infrared light range, at least one temperature sensor, and at least one impedance sensor.

15. The ingestible pill of claim 1, wherein the at least one radioactive-emission detector for detecting pathologies in the colon is further configured as an imager, for imaging pathologies in the colon, as a function of position along the colon.

16. The ingestible pill of claim 1, configured for contracting under the pressure of the external anal sphincter muscle, for elimination of the ingestible pill from the living being.

17. The ingestible pill of claim 1, wherein the body further includes a core and the outer portion of the ingestible-pill body comprises a stretchable skin surrounding the core and expansion mechanism.

18. The ingestible pill of claim 1, wherein the at least one radioactive-emission detector is adapted to be moved by the expansion mechanism.

19. The ingestible pill of claim 1 wherein the at least one radioactive-emission detector comprises at least two detectors adapted to be moved away from each other by the expansion mechanism.

20. A method of colon recognition, by an ingestible pill, comprising:
providing an ingestible pill, which comprises:
an ingestible-pill body, adapted to be swallowed by a living being and adapted for traveling down a gastrointestinal tract of the living being, the body including an expansion mechanism and an outer portion including a part which includes at least one radioactive-emission detector for detecting pathologies in the colon, wherein the outer portion comprises a skin which contacts the at least one radioactive-emission detector; and
a colon-recognition trigger mechanism, associated with the ingestible-pill body and configured to produce a colon-entry signal, when the ingestible-pill body enters the colon of the living being;
administering the ingestible pill to the living being;
recognizing colon-entry by the colon-recognition trigger mechanism;
producing the colon-entry signal, upon the recognizing; and
expanding the expansion mechanism, thereby moving said part of said outer portion relative to an opposite part of the outer portion.

21. The method of claim 20, wherein the colon-recognition trigger mechanism is selected from the group consisting of:
an ultrasound sensor, configured to produce the colon-entry signal, based on the difference in structure between the small intestine and the colon,
an MRI sensor, configured to produce the colon-entry signal, based on the difference in structure between the small intestine and the colon,
a video camera, configured to produce the colon-entry signal, based on the difference in structure between the small intestine and the colon,
an ultrasound sensor, configured to produce the colon-entry signal, upon imaging the semilunar fold structure, which is unique to the colon,
an MRI sensor, configured to produce the colon-entry signal, upon imaging the semilunar fold structure, which is unique to the colon,
a video camera, configured to produce the colon-entry signal, upon imaging the semilunar fold structure, which is unique to the colon, a radioactive-emission sensor, configured to produce the colon-entry signal, upon functional sensing the generally inflammatory state of the vermiform appendix, an optical-fluorescence-spectroscopy sensor, configured to produce the colon-entry signal, upon functional sensing the generally inflammatory state of the vermiform appendix, a pH sensor, configured to produce the colon-entry signal, upon sensing the pH environment of the colon, which is greater than 7, an enzyme sensor, configured to produce the colon-entry signal, upon sensing the enzyme environment of the colon, a chemical sensor, configured to produce the colon-entry signal, upon sensing the chemical environment of the colon, a bacterial sensor, configured to produce the colon-entry signal, upon sensing the flora environment of the colon, and a combination of the above.

22. The method of claim 20, wherein expanding the expansion mechanism comprises expanding the expansion mechanism, thereby expanding the ingestible pill body into an expanded structure, having expanded length and width parameters, which are between a factor of two and a factor of five greater than the initial length and width parameters, so as to push the outer portion in an outward direction from the center of the body, when the colon-recognition trigger mechanism produces the colon-entry signal.

23. The method of claim 22, wherein the expanded structure has a shape, selected from the group consisting of an elliptical capsule, a plurality of loops, a star fish, and a plurality of spines.

24. The method of claim 22, and further including detecting pathologies in the colon, by the expanded structure.

25. The method of claim 24, and further including imaging pathologies in the colon, as a function of position of the ingestible pill along the colon.

26. The method of claim 20, wherein the expansion mechanism is an absorption mechanism, selected from the group consisting of the absorption of gastrointestinal fluids by osmosis, the absorption of gastrointestinal fluids by a foam, the absorption of gastrointestinal fluids by guar gum, the absorption of gastrointestinal fluids by polyacrylic acid, the absorption of gastrointestinal fluids by a hydrogel, the absorption of gastrointestinal fluids by hydroxypropylmethylcellulose-HPMC, the absorption of gastrointestinal fluids by polyethylene oxide, the absorption of gastrointestinal fluids by Laminaria digitata, the absorption of gastrointestinal fluids by Laminaria japonica, a combination of the above.

27. The method of claim 20, wherein the ingestible pill expands generally uniformly.

28. The method of claim 20, and further including contracting under the pressure of the external anal sphincter muscle, for elimination of the ingestible pill from the living being.

* * * * *